United States Patent [19]

Flood et al.

[11] 4,305,816
[45] Dec. 15, 1981

[54] APPARATUS AND METHOD FOR INSPECTING CONTAINERS

[75] Inventors: John M. Flood; Charles W. Scharf, both of Randolph; James D. Alexander, Jamestown, all of N.Y.

[73] Assignee: Borden, Inc., Columbus, Ohio

[21] Appl. No.: 120,526

[22] Filed: Feb. 11, 1980

[51] Int. Cl.³ .............................................. B07C 5/344
[52] U.S. Cl. .................................... 209/549; 209/577; 209/588
[58] Field of Search ............... 209/555, 556, 557, 576, 209/577, 588, 597, 546, 549, 551, 565; 356/237

[56] References Cited

U.S. PATENT DOCUMENTS

| | | |
|---|---|---|
| Re. 25,671 | 10/1964 | Larew et al. . |
| 901,393 | 10/1908 | Sleeper . |
| 1,922,188 | 8/1933 | Zworykin . |
| 2,070,339 | 2/1937 | Moore . |
| 2,229,451 | 1/1941 | Gulliksen . |
| 2,244,228 | 6/1941 | Weitmann . |
| 2,318,856 | 5/1943 | Hoffman . |
| 2,332,308 | 10/1943 | Dresser . |
| 2,395,181 | 2/1946 | Hags . |
| 2,395,482 | 2/1946 | Hurley, Jr. . |
| 2,453,720 | 11/1948 | Meister . |
| 2,524,929 | 10/1950 | Razek . |
| 2,551,020 | 5/1951 | Laxo . |
| 2,570,288 | 10/1951 | Todd . |
| 2,612,815 | 10/1952 | Britt . |
| 2,696,106 | 12/1954 | Schneider . |
| 2,729,136 | 1/1956 | Feick et al. . |
| 2,742,151 | 4/1956 | Milford . |
| 2,750,519 | 6/1956 | Summerhayes, Jr. et al. . |
| 2,820,908 | 1/1958 | Linderman . |
| 2,872,039 | 2/1959 | Lynn et al. . |
| 2,886,716 | 5/1959 | Camp . |
| 2,902,151 | 9/1959 | Miles et al. . |
| 2,939,016 | 5/1960 | Cannon . |
| 3,070,227 | 12/1962 | Larew et al. . |
| 3,085,160 | 4/1963 | Dahms . |
| 3,105,151 | 9/1963 | Nash . |
| 3,218,463 | 11/1965 | Calhoun . |
| 3,302,787 | 2/1967 | Rottmann . |
| 3,349,906 | 10/1967 | Calhoun . |
| 3,355,980 | 12/1967 | Mathias . |
| 3,356,853 | 12/1967 | Rottmann . |
| 3,379,829 | 4/1968 | Gambrell et al. . |
| 3,394,263 | 7/1968 | Baker . |
| 3,395,285 | 7/1968 | Scanlon et al. . |
| 3,406,822 | 10/1968 | Finger et al. . |
| 3,415,370 | 12/1968 | Husome . |
| 3,416,659 | 12/1968 | Linderman et al. . |
| 3,418,482 | 12/1968 | Masson . |
| 3,453,054 | 7/1969 | Phillips . |
| 3,462,015 | 8/1969 | Tysver et al. . |
| 3,479,514 | 11/1969 | Kidwell . |
| 3,479,518 | 11/1969 | Akamatsu et al. . |
| 3,481,467 | 12/1969 | Wood . |
| 3,533,704 | 10/1970 | Krenmayr . |
| 3,557,950 | 1/1971 | Powers . |
| 3,564,269 | 2/1971 | Lynch . |
| 3,586,168 | 6/1971 | Osheff et al. ................... 209/551 X |
| 3,631,255 | 12/1971 | Gender et al. . |
| 3,680,966 | 8/1972 | Cofek . |
| 3,750,877 | 8/1973 | Dvacho et al. .................... 209/588 |
| 3,757,940 | 9/1973 | Damm ............................ 209/565 X |
| 3,757,943 | 9/1973 | Chae et al. .......................... 209/551 |
| 3,778,617 | 12/1973 | Chalhoun . |
| 3,826,923 | 7/1974 | Trimble et al. . |
| 3,851,975 | 12/1974 | Serret . |
| 4,074,809 | 2/1978 | McMillin et al. .................. 209/588 |
| 4,105,122 | 8/1978 | Flood et al. ......................... 209/556 |

Primary Examiner—Robert J. Spar
Assistant Examiner—Edward M. Wacyra
Attorney, Agent, or Firm—Millard & Cox

[57] ABSTRACT

Method and apparatus for testing open ended containers wherein the open ends of the containers are clamped against regularly spaced apertures in a carrier wheel and are rotated along a locus leading across two spaced inspection stations. Lighting is provided principally along the container sidewall leading with respect to the direction of its locus of movement within the first inspection station environment and is provided principally along a sidewall considered lagging as the container passes the second inspection station. Defect responsive photosensing signals from the two stations are submitted to OR logic sequential memory to syncronize the operation of a discharge carrier. No vacuum retention of the containers within the transfer disc region is required.

40 Claims, 26 Drawing Figures

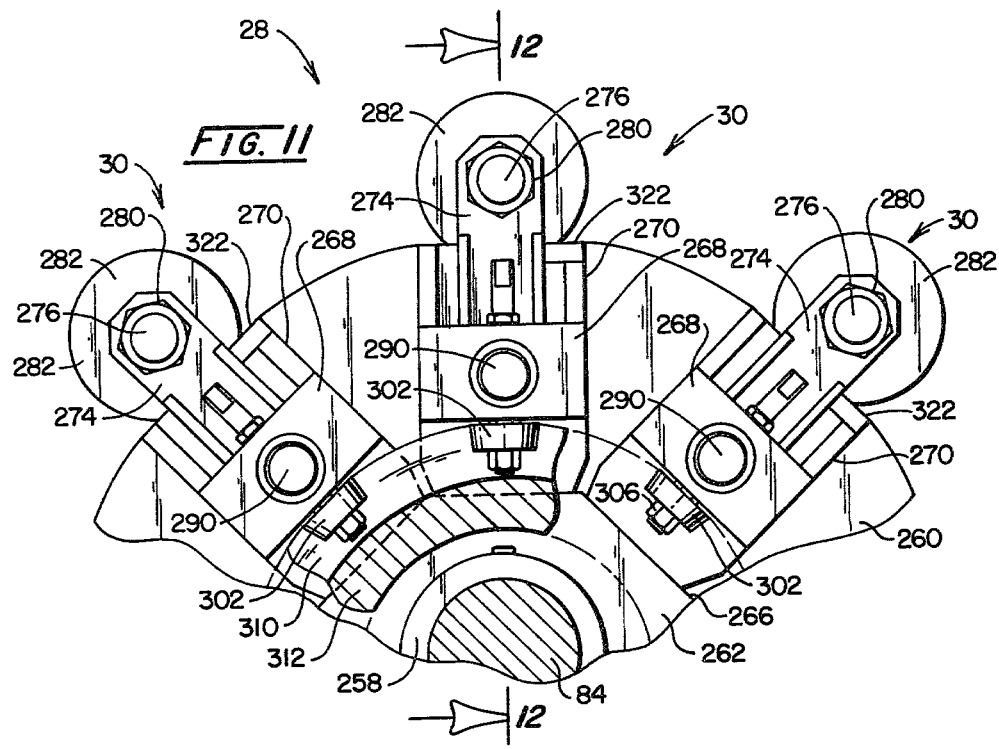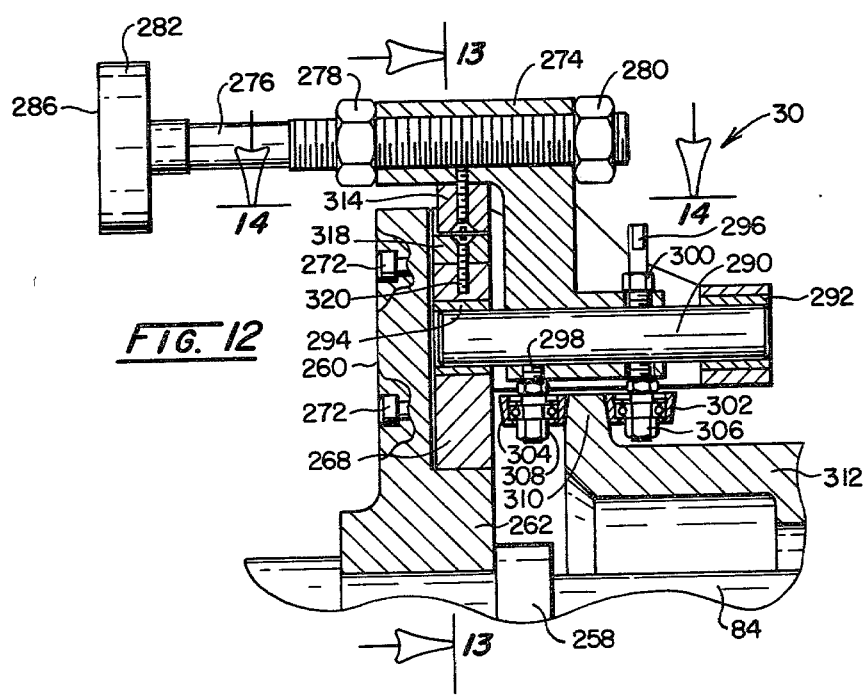

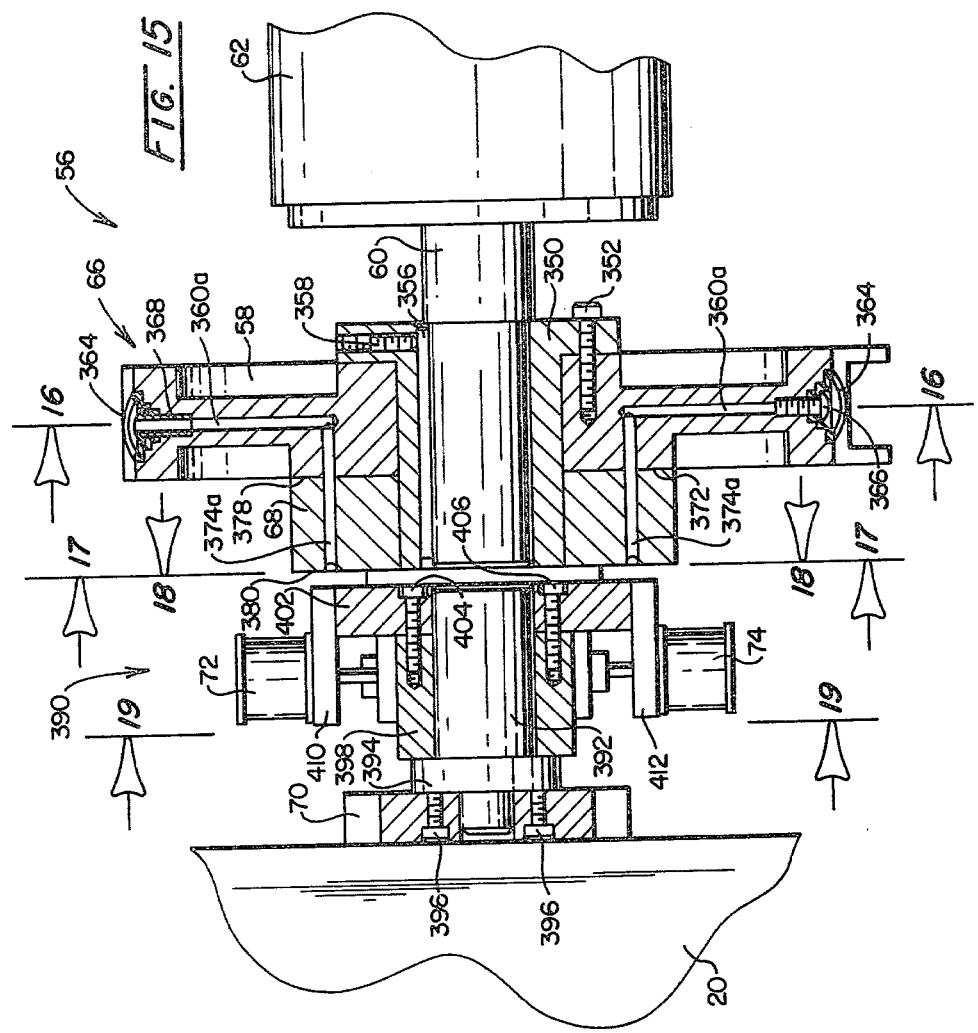

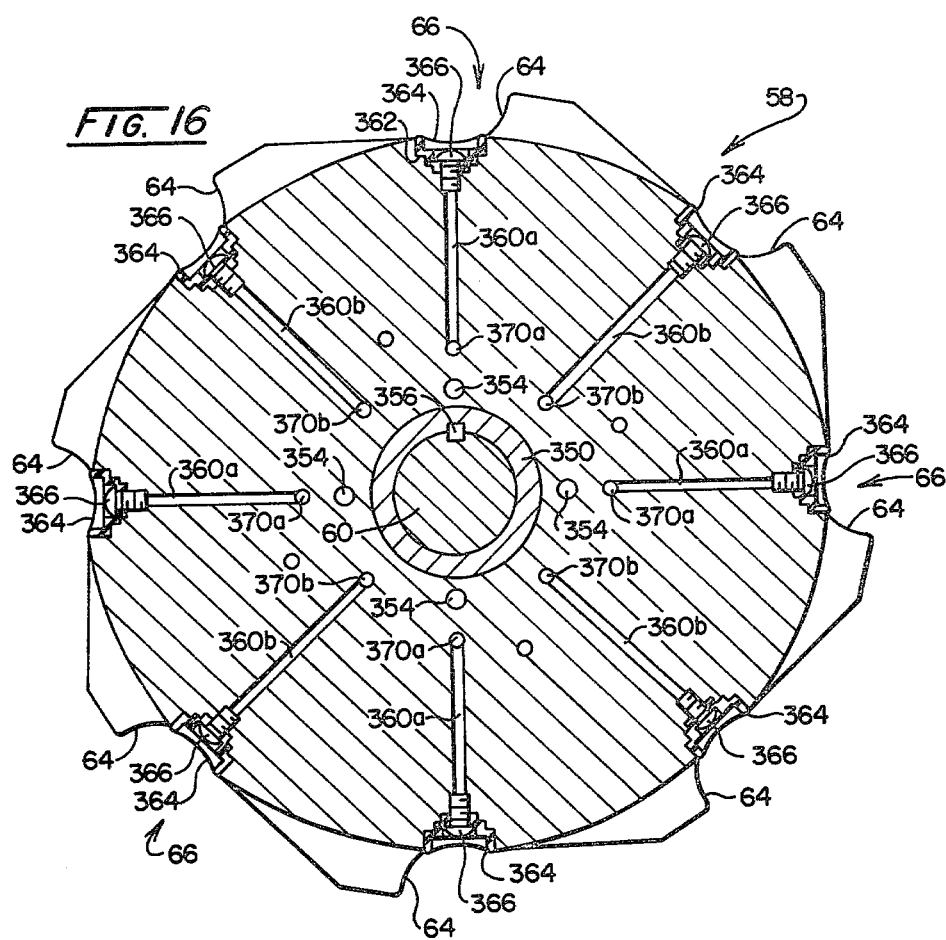
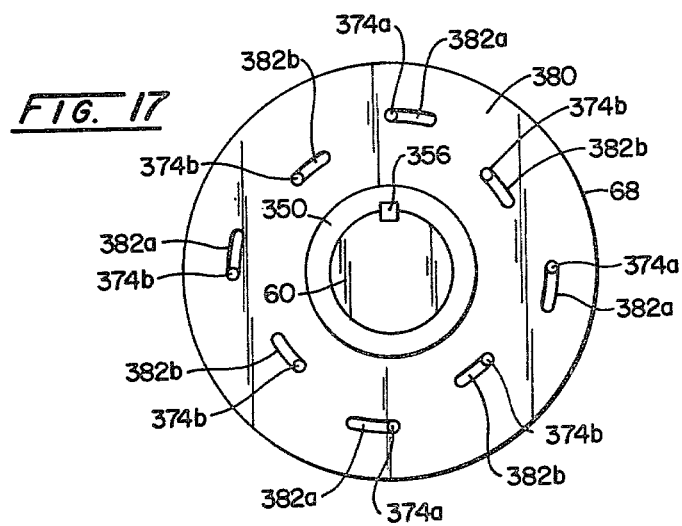

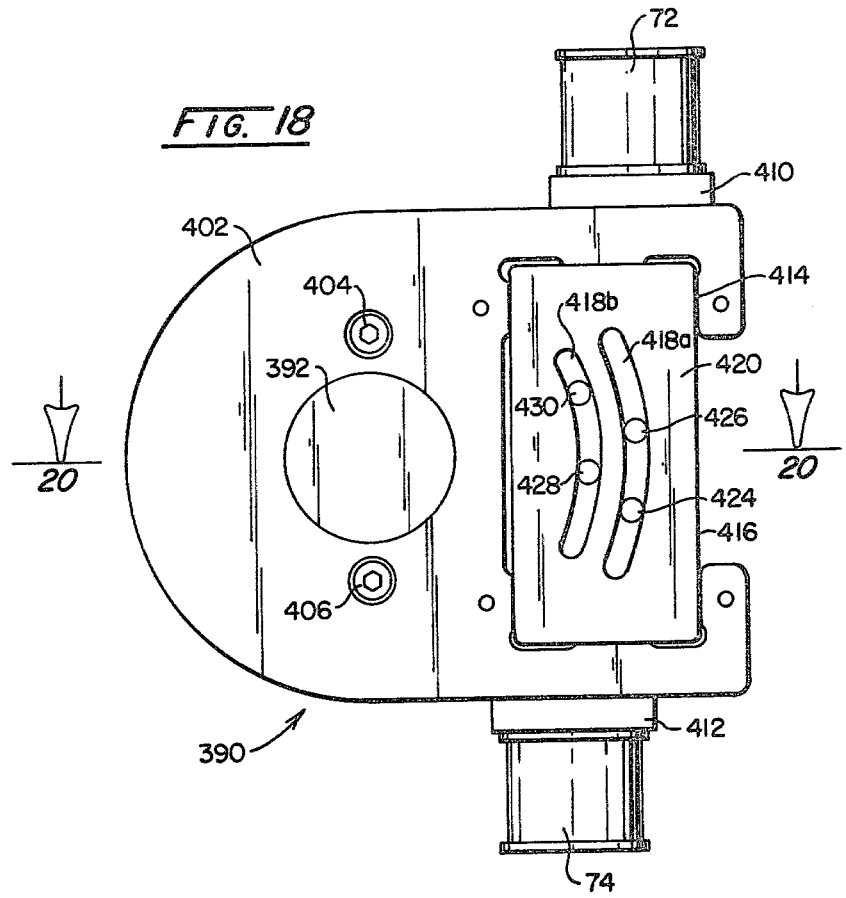
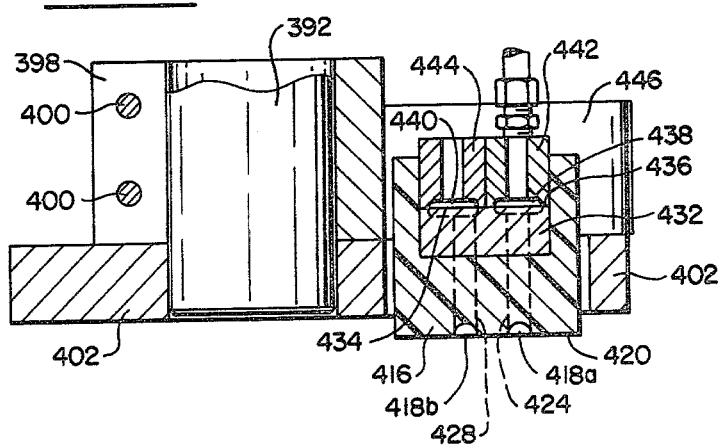

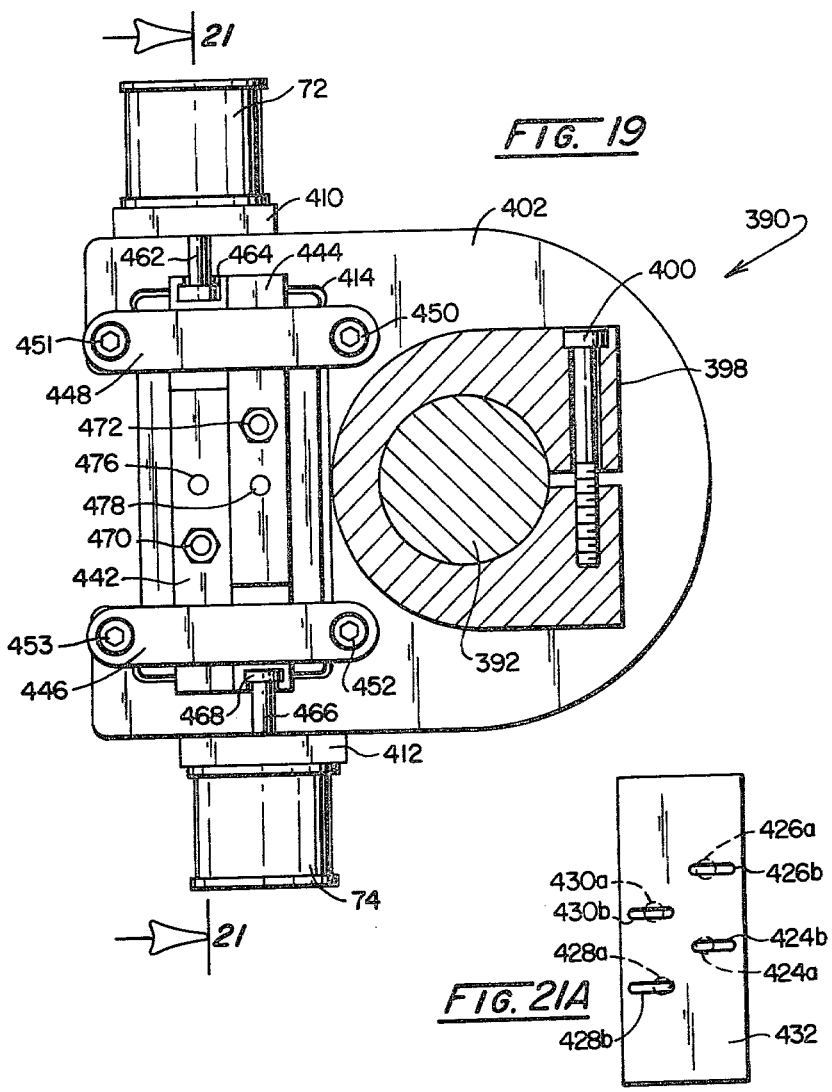
FIG. 19
FIG. 21A
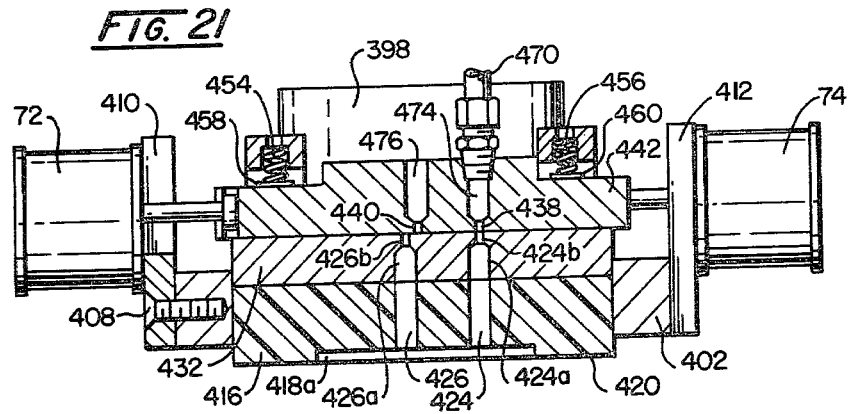
FIG. 21

APPARATUS AND METHOD FOR INSPECTING CONTAINERS

BACKGROUND OF THE INVENTION

A widespread public acceptance of aluminum containers, the principal body portions of which are drawn from disk stock using high volume production techniques has led to a concomitant need for reliable, high-speed testing devices. Such testing as carried out by the devices serves to assure the wall integrity of the cans or containers, thus permitting their more predominant usage, the packaging of food products. The presence of defects, for example in the form of pinhole openings or minute cracks, may lead to contamination and spoilage, not only in connection with the contents of defective containers or cans, but also in connection with adjacently packaged containers.

The initial approach utilized in testing the container bodies was one of carrying out pressure testing, for example as disclosed in U.S. Pat. No. 3,750,348 by Masservey et al. While effective, such testing procedures necessarily are slower and require the use of somewhat elaborate machinery. Maintenance costs for the apparatus carrying out air testing are considered to be high as well as is the cost, in and of itself, of pumping air, as well as in the maintenance of rubber pads, air cylinders and the like, all of which are required in the development of a high speed test approach.

Over the more recent past, designers of container testing equipment have looked to the utilization of light as the testing medium, a photoresponsive component being associated with the interior of can bodies, while the exterior surfaces of the cans are flooded with light.

The general approach to providing high speed light testing systems has been to provide a continuously rotating transfer apparatus having successive cradles or pockets within which the can bodies to be tested are deposited in a horizontal orientation, their open ends facing forwardly. An aperture containing wheel corotates with the apparatus, one aperture of a plurality thereof being aligned axially with each can body. As the transfer apparatus rotates, a reciprocally movable holding device which co-rotates with the transfer apparatus and somewhat resembles a piston, contacts the bottom wall of each can body, connects itself thereto through a vacuum port and pushes the can body into the aperture containing wheel in a manner wherein the rim of the can surmounting its open end is urged into contact with a seal at the wheel such that it surrounds an associated aperture. The transfer apparatus continues to rotate and reaches an inspection station whereat all the external surfaces of the can body are illuminated with light of substantially uniform intensity and a photosensitive device positioned within the locus of travel of the can and associated aperture but on the opposite side of the aperture containing wheel is positioned to detect the passage of light through defects within the can body. Upon detecting a defect derived quantum of light within the can body interior, the photoresponsive device develops a signal which is used to discharge the can into a reject channel following further transfer apparatus rotation. Generally, the removal of cans from the transfer apparatus takes place by retracting the holding device while maintaining vacuum connection with the can bottom wall and then terminating the vacuum connection at a proper position, for example at the entrance of a discharge chute. To prevent damage to the can body members as they are urged forwardly and retained against the aperture containing wheel, generally the vacuum holding devices are made yieldable through compression springs or the like. Examples of such devices are revealed in U.S. Pat. No. 3,750,877 by Dvacho et al and U.S. Pat. No. 4,074,809 by McMillin et al.

Another approach to high speed light testing of can bodies is described in U.S. Pat. No. 4,105,122 by Flood et al. In this apparatus, the rotating test carriage is eliminated, the can bodies being fully retained in position by extensible and retractable vacuum connecting holder devices. With the arrangement, the cans are positioned in an in-feed star wheel device and held by vacuum as well as compression against a series of photosensitive stations positioned within a corotating test wheel. Removal of the can body members is by a cooperating discharge star wheel either to a defective can discharge region or to the threshold of a discharge chute. The photosensitive devices used in the testing procedure are designed to provide scrutiny for defects within the can body portion itself as well as in the region of the flange extending from the rim about the open end of the can.

While the above-described testing techniques and associated apparatus represent significant advances in testing technology, improvements looking to the simplification of machinery while maintaining test reliability will be welcomed by industry.

SUMMARY OF THE INVENTION

The present invention is addressed to an improved apparatus and method for testing open ended containers for defects in the form of openings in their structure. With the apparatus, the containers are clamped in continuous sequence within a rotating test carrier such that their open ends are located over apertures formed in a predetermined pattern within a transfer component which may be present in disk shape or wheel form. Clamping engagement of the cans is only by the compressive maintenance of the cans from their bottom portion against the transfer disk. No vacuum retention is provided or required. Rotation of the carrier and disk moves the thus clamped containers across two spaced and illuminated inspection stations, each station incorporating a photosensitive device. The latter devices derive separate output signals upon exposure to light passing through a container body portion defect. A discharge arrangement is provided which is normally operative to receive each of the container body portions. When the compressive clamping thereof is removed by retraction, this discharge arrangement further is actuable to negate container reception for the purpose of sorting defect-containing containers from those passing the inspection test. A control circuit is provided which is responsive to each output signal derived from the two inspection stations and serves to OR these signals to carry out the properly synchronized actuation of the discharge arrangement. Movement of the container bodies from the transfer arrangement takes place without a specific instrumentality and in consequence of the dynamics inherent within the testing apparatus itself. Rearward movement from the container rim positioning against the test disk is evolved, in part, because of a rearwardly directed vector developed by virtue of the thicker metal structure and consequent heavier weight of the container bottoms as opposed to their thin sidewall structure.

As another feature and object of the invention, the light sources provided in connection with each of the two inspection stations are positioned to illuminate predetermined portions of a container body. For example, when the containers approach and pass through the first of the inspection stations, illumination is provided principally at the sidewall portion of the container which is leading with respect to the direction of its locus of movement. Conversely, as the container body portion approaches and passes through the second inspection station, the light sources are positioned as so to illuminate principally the sidewall portion of a container which is considered lagging with respect to the direction of its locus of movement. The combination of such lighting and dual inspection stations achieves a desirable testing reliability while minimizing lighting power requirements for the test technique and apparatus.

As another object of the invention, the discharge component of the apparatus is formed including a star wheel incorporating discrete cradles within which container body portions are received. Retention of these containers is through a vacuum port positioned within each cradle in a manner wherein contact is made with each container essentially at a point midway along its sidewall. Where the containers are deformed, such attachment will not be made and the deformed containers inherently are discharged from the apparatus as defects without additional testing scrutiny.

Another object of the invention is to provide apparatus for automatically testing open ended containers for defects in the form of openings in their structure, these containers having an opening surmounted by a rim and a sidewall portion extending from that rim to a bottom portion. The apparatus includes a supportive frame upon which a shaft is rotatably supported and which has a generally horizontally disposed axis of rotation. A transfer arrangement is fixed to and rotatable with the shaft which has a plurality of apertures therein which are regularly spaced about the periphery of the transfer component, which may have a flat disk or wheel shape. The apertures are configured in correspondence with the configuration of the container rim portions and serve to selectively receive the containers in abuttive relationship at a contact surface portion surrounding the periphery of the aperture. A holder arrangement is provided which includes a plurality of reciprocative retention components corresponding in number with the number of the apertures and mounted for rotation with the shaft at locations spaced from and disposed opposite corresponding ones of the apertures. Each of the retention components includes a contact member which is extensible into abutting engagement with a container bottom portion to compressibly urge the rim of the container into light-tight abutting engagement with the transfer arrangement contact surface and is retractable from that abutting engagement to effect a release from the container bottom portion. A first inspection station is mounted upon the frame adjacent to, stationary with respect to and in light-tight communication with the transfer component and includes a first photosensitive device located for successive alignment with each aperture and the container opening associated therewith for deriving a first output signal upon exposure to light passing through a defect within a container. A second inspection station, which is spaced from the first inspection station, is mounted upon the frame adjacent to, stationary with respect to and in light-tight communication with the rotatable transfer component and which includes a second photosensitive device located for successive alignment with each aperture and the container opening associated with that aperture, for deriving a second output signal upon exposure to light passing through a container defect. A first light source is provided for illuminating the exterior of containers when passing the first inspection station and a second light source is provided for illuminating the exterior of containers when passing the second inspection station. Infeed components are provided for feeding containers intermediate the holder retention components and the transfer arrangement contact surfaces. A discharge apparatus is provided which is normally operative to receive each container when the reciprocative retention component contact member associated therewith is retracted and which is actuable to negate that container reception. A control arrangement which is responsive to the first and second output signals is provided for actuating the discharge apparatus to negate the reception of a defect containing container. A drive arrangement is provided for drivably rotating the shaft to carry out inspection.

Another object of the invention is to provide a method for testing open-ended containers for defects in the form of openings in their structure, the containers having an opening surmounted by a rim and a sidewall portion extending from the rim to a bottom portion. The method includes the steps of positioning the openings of a continuous sequence of the containers over apertures extending through a transfer member rotating with a test carrier and defining a predetermined locus of movement of the apertures. The container rims are compressively retained in light-tight relationship against the rotating support by applying a contact member against their bottom portions. A first light detecting device is provided at a first station positioned adjacent the rotating support at the locus of movement of the aperature, the interior of a container being exposed to the first light detecting device through an aperture when moved across the first station. The container sidewall portion leading with respect to its locus of movement is illuminated principally with the device. A first output signal is generated in response to light passing through a defect in the container structure and impinging upon the first light detecting device. A second light detecting device is provided at a second station positioned adjacent the rotating support at the locus of movement of the container aperture, the interior of the container being exposed to the second light detecting device through the aperture associated therewith when moved across the second station. The sidewall portion of the container lagging with respect to the direction of its locus of movement is illuminated principally when that container is moved across the second station. A second output signal is generated in response to light passing through a defect within the container and impinging upon the second light detecting device and the containers are sorted in response to the first or second output signals such that those having a detected defect are separated from those not having a detected defect.

Still another object of the invention is to provide apparatus for automatically testing open ended containers as described above incorporating a control system which includes an encoder responsive to the rotation of the carrier disc or shaft associated therewith of the apparatus to derive a clock signal corresponding with the position of each of the carrier disk apertures as each such aperture passes a predetermined reference position. This position may, for example, be the vertical intersect between the first and second inspection stations. A first AND logic network is provided which is responsive to the first output signal of the first station photoresponsive device. A second AND logic network is provided which is responsive to the second output signal of the second photosensitive device and the first and second AND logic means, respectively, derive first and second defect signals. A sequential storage arrangement is provided in the form of a shift register which is responsive to the clock signal and is provided having a first input zone for receiving the first defect signal and a first output for deriving the first defect signal in time synchronization correspondence with the distance between the first and second inspection stations. OR logic is provided which is responsive to the time synchronized first defect signal and/or the second defect signal for providing an OR logic output. The sequential storage means further include a second input zone for receiving the OR logic output and a second output zone for deriving a composite defect signal in time synchronism correspondence with the distance between the second inspection station and the predetermined position of the discharge component at which the discharge component communicates with an off-loading conveyor. A switching network is provided which is responsive to the composite defect signal for actuating the discharge component to carry out a rejection of a container containing defects. Preferably, two vacuum circuits are used in connection with the discharge component and which are associated with every other aperture position on the carrier disk.

Other objects of the invention will, in part, be obvious and will, in part, appear hereinafter.

The invention, accordingly, comprises the apparatus and method possessing the construction, combination of elements, arrangement of parts and steps which are exemplified in the following detailed disclosure. For a fuller understanding of the nature and objects of the invention, reference should be had to the following detailed description taken in conjunction with the accompanying drawings.

BRIEF DESCRIPTION OF THE DRAWINGS

FIG. 11 is a partial sectional view taken through the plane 11—11 of FIG. 3;

FIG. 12 is a partial sectional view taken through the plane 12—12 in FIG. 11;

FIG. 15 is a partial sectional view taken through the plane 15—15 of FIG. 2;

FIG. 16 is a partial sectional view taken through the plane 16—16 in FIG. 15;

FIG. 17 is a partial sectional view taken through the plane 17—17 of FIG. 15;

FIG. 18 is a partial sectional view taken through the plane 18—18 of FIG. 15;

FIG. 19 is a partial sectional view taken through the plane 19—19 in FIG. 15;

FIG. 20 is a partial sectional view taken through the plane 20—20 in FIG. 18;

FIG. 21 is a partial sectional view taken through the plane 21—21 in FIG. 19;

FIG 21A is a top view of component 432 of the assembly shown in FIG. 21;

DETAILED DESCRIPTION

Figure 1:
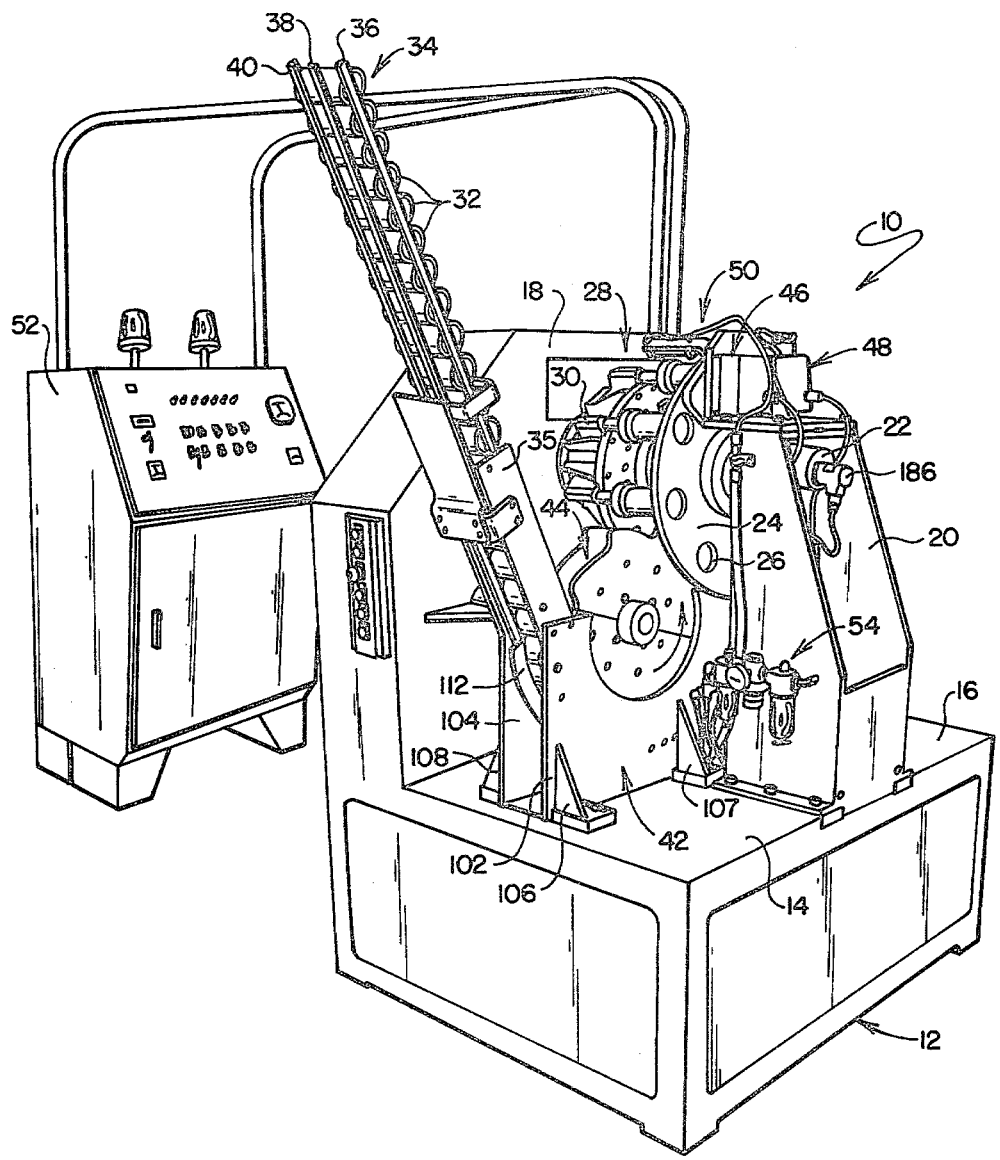
FIG. 1 is a pictorial representation of apparatus for testing open-ended containers according to the invention.
Figure 3:
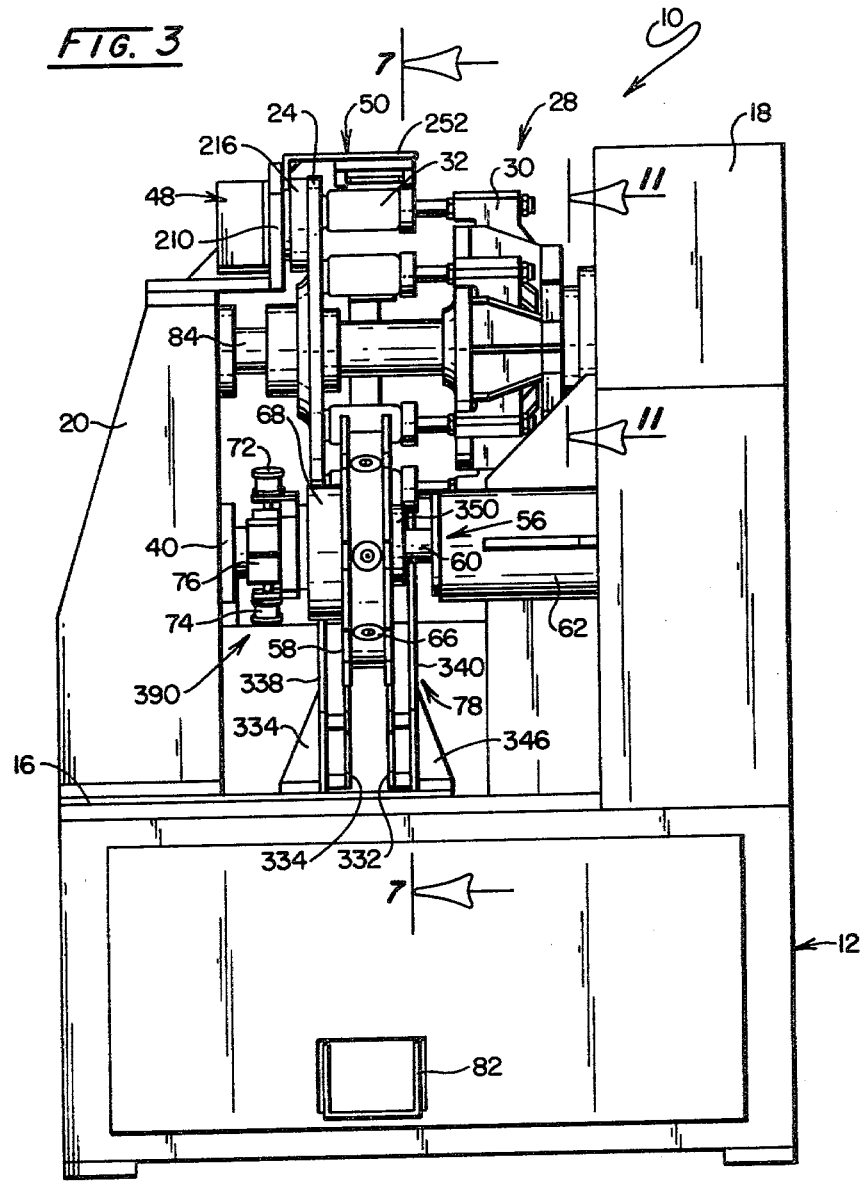
FIG. 3 is a rear elevational view of the apparatus of FIG. 1.

In general, a preferred embodiment for the apparatus of the invention is revealed pictorially at 10 in FIG. 1. Apparatus 10 includes a lower frame assembly 12 formed of rigid angle stock and which is surmounted by top plates 14 and 16. Frame 12 additionally extends upwardly at 18 and is provided sidewalls so as to define an enclosure for retaining drive components and a bearing supported a driven shaft 84 extending horizontally along the center of the upward portion of the frame (FIG. 3). The opposite end of this horizontal shaft is supported by a pedestal 20 through journaled association with a bearing described at 158 in connection with FIG. 6. This bearing is mounted behind enclosure 22. Mounted upon the central horizontally oriented shaft is a carrier disk or wheel 24 within which are formed a plurality, for example 8, apertures, certain of which are revealed at 26. Disk 24 is of annular configuration and the circular apertures 26 formed therein are associated with a sealing structure which serves to provide a contact surface as well as define a round opening of a diameter slightly less than the diameter of the openings of the containers 32 being tested. These containers 32 are shown in an infeed portion of the apparatus 10 being clamped or compressibly urged against the noted contact surfaces at carrier disk 24 by a holder arrangement shown generally at 28 rotatable with the assemblage and including a plurality of reciprocative retention components 30.

Containers 32 are fed to apparatus 10 along a gravitational infeed chute 34 formed, inter alia, of rails 36, 38 and 40. Infeed chute 34 extends to and is connected with an infeed guide structure shown generally at 42 which serves to align incoming containers 32 in a manner permitting their reception by an infeed star wheel structure 44 which receives the containers 32 in cradles formed therein. Wheel 44 rotates in the direction indicated by the arrow to present container 32 at an input position intermediate the reciprocative retention components 30 and the contact surfaces at an appropriately aligned aperture 26. Thus, the containers 32 are carried rotationally inwardly from this input positon, whereupon the interior cavities thereof are inspected at two spaced inspection stations represented generally at 46 and 48. A lighting arrangement is associated with each of these inspection stations inwardly of disk 24 in the general region 50. FIG. 1 further depicts a control console for the apparatus 10 at 52, while compressed air treating components for use in connection with an air brake described later herein are represented generally at 54.

Figure 2:
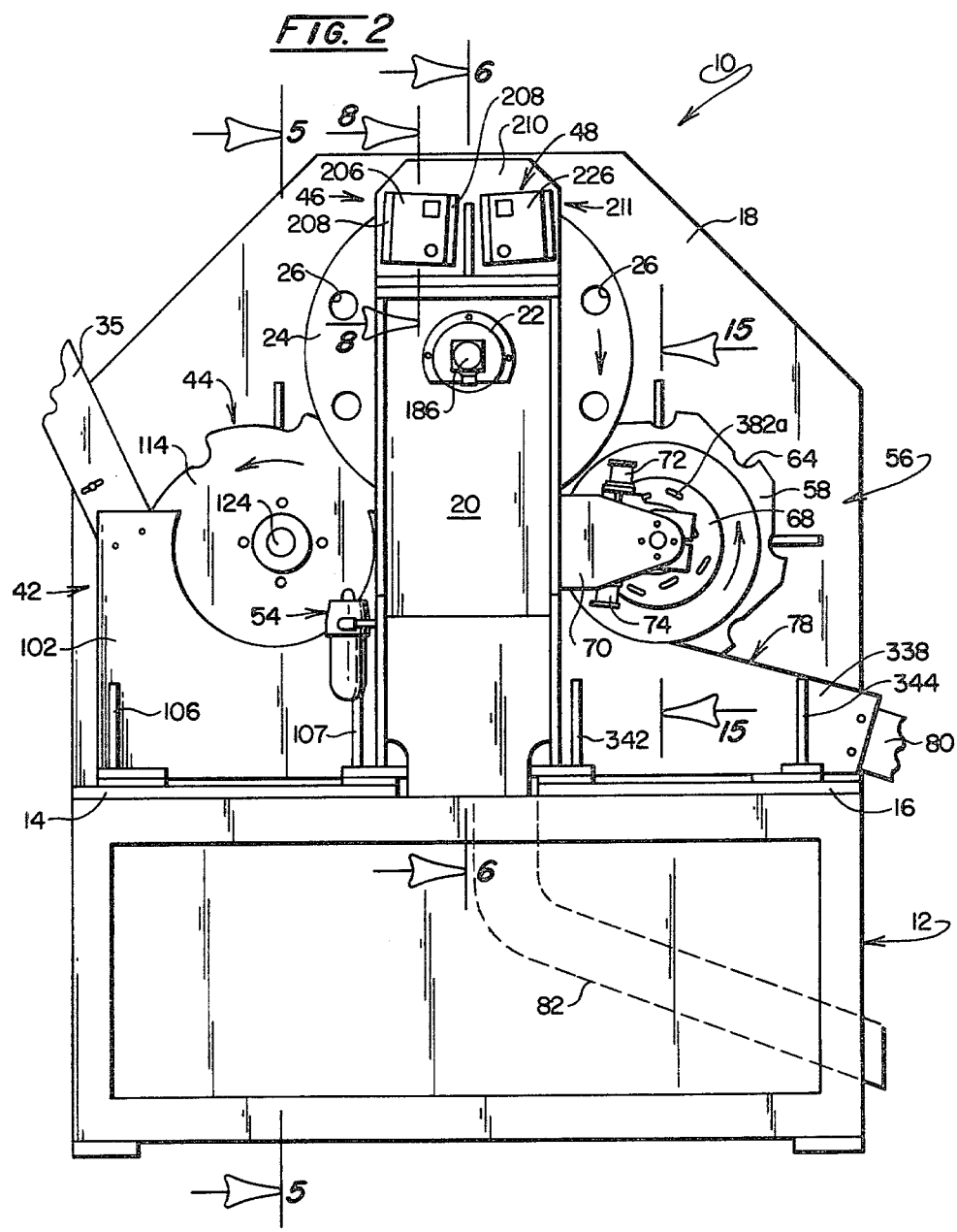
FIG. 2 is a right side elevational view of the apparatus of FIG. 1.

Looking additionally to FIGS. 2 and 3, the discharge components of assembly 10 are revealed generally at 56. These components include a discharge star wheel 58 rotating in the direction shown by the arrow and drivably supported by a shaft 60 extending outwardly from a support cylinder 62 which, in turn, extends from upward frame portion 18. Controlled rotational drive is provided shaft 60 from drive components described later herein. Star wheel 58 is formed having a series of peripherally disposed cradles 64, each of which extends over a vacuum port assembly, certain of which are shown generally at 66 in FIG. 3. These port assemblies 66 cooperate with a vacuum supply control manifold 68 and a valve arrangement 76 the latter being supported from bracket 70. Solenoids as at 72 and 74 form part of the valve assembly supported by bracket 70. Discharge wheel 58 serves to remove containers 32 from the apparatus 10 inspection function by a cooperative association between the cradles 64 thereof with transfer disk 24 and associated holder 28. Reception of container 32 by wheel 58 takes place about 45° below horizontal as taken through the axis of shaft 84 and at this position a sorting function is carried out wherein containers having no detected defect are directed along a discharge guide fixture 78 attached to top plate 16 to a discharge chute a portion of which is revealed at 80. Defective containers are not accepted by the apparatus 56 and are dropped into defective container discharge chute 82.

Figure 8:
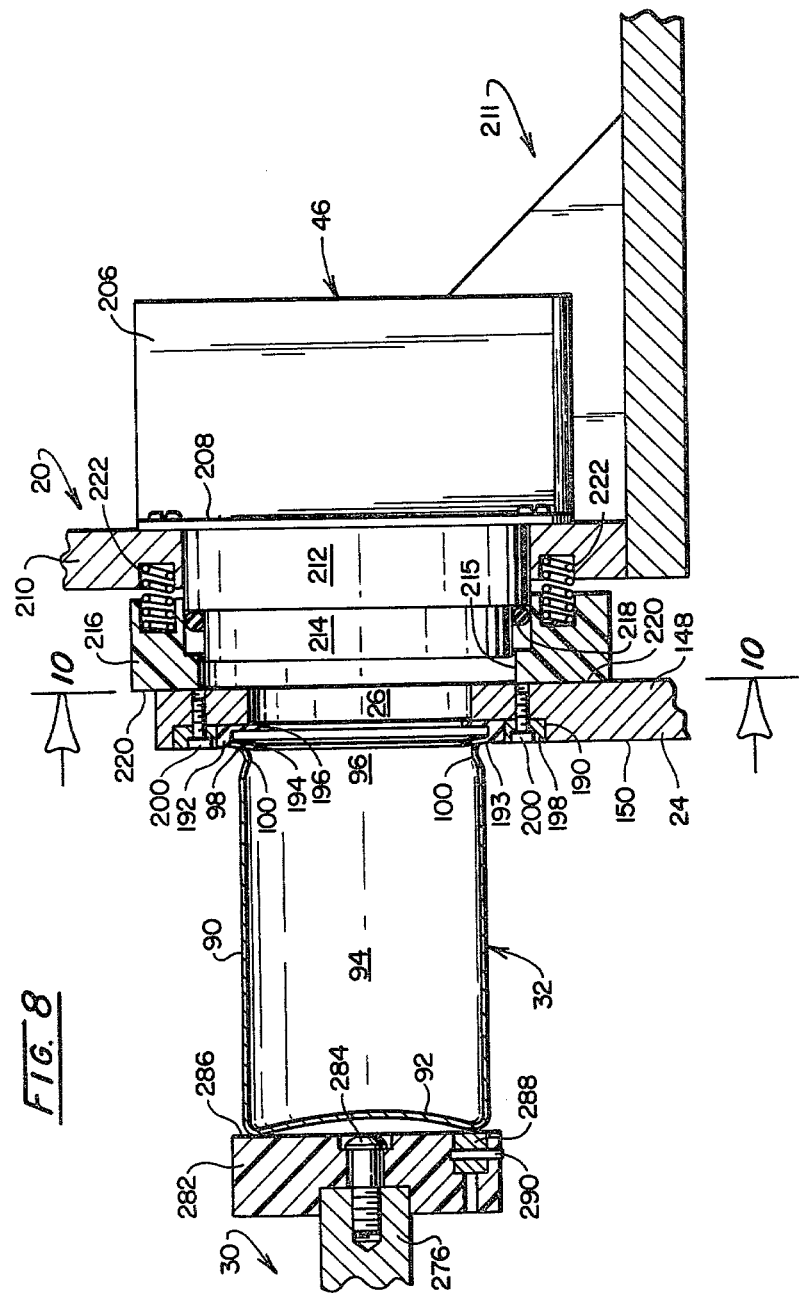
FIG. 8 is a partial sectional view taken through the plane 8—8 of FIG. 2.

While the containers as shown at 32 may assume a variety of open-ended configuration, the inventive concepts herein described look to an apparatus for testing any tubular member for sidewall and bottom portion defects such as pinholes and the like such as cracks which are amenable to the instrusion of externally supplied light. The instant invention, however, is particularly adapted for testing the single piece body members as represented in several of the drawings at 32 which are utilized for the manufacture of two-piece aluminum cans. As shown in FIG. 8, such one-piece aluminum can body components comprise an annular sidewall portion 90, which is closed at one end by an inwardly domed concave bottom portion 92 to define a container cavity 94. Sidewall portion 90 extends from bottom portion 92 to an opening 96 surmounted by a rim 98. Generally, rim 98 extends somewhat radially outwardly to define a flange portion 100 and this outwardly contoured structure of rim 98 is specifically taken account of with the instant invention, as is described later herein. Such can body members or containers 32, conventionally, are utilized to package beer, soft drinks, and other products by filling the container cavity 94 with the product and then attaching an end closure over the opening 96 in sealed association with the flange portion 100, which is further deformed during the attachment process to effect a sealed relationship with the rim 98.

The defects for which inspection is carried out include pinholes or cracks which may have a diameter or width as small as 0.001 inch as well as any dents or deformations in the sidewall portion 90 itself. Because the cans 32 are formed from disk stock using high volume drawing techniques and the like, the bottom portion 92 generally will be thicker than the sidewall portions 90. Thus the former bottom region of the container 32 is heavier or more dense and this characteristic of the cans is taken advantage of by the apparatus 10 to achieve highly desirable simplification of the container manipulation procedure.

In the discourse to follow, the individual components of apparatus 10 are considered in detail under appropriate sub-headings. Following such discussions, a description of the general operation and methodology of the apparatus is set forth.

Infeed Structure

As described in connection with FIG. 1, a continuous supply of containers 32 is provided from a generally overhead location by an infeed chute 34 formed principally of guide rails, a side rail thereof being shown at 36 and bottom guide rails being represented at 38 and 40. These rails communicate with a second infeed guide arrangement represented generally at 35 which, in turn, is coupled to spaced parallel side guides 102 and 104 of infeed guide structure 42. Referring to FIGS. 1, 2, 5 and 7, side guides 102 and 104 are shown to be coupled to top plate 14 of the frame 12 by brackets 106–109. As is revealed more clearly in FIGS. 5 and 7, side guides 102 and 104 further support respective arcuately shaped guide rails 110 and 112 which serve to retain the containers 32 in position against cradles within infeed star wheel 44.

Figure 5:
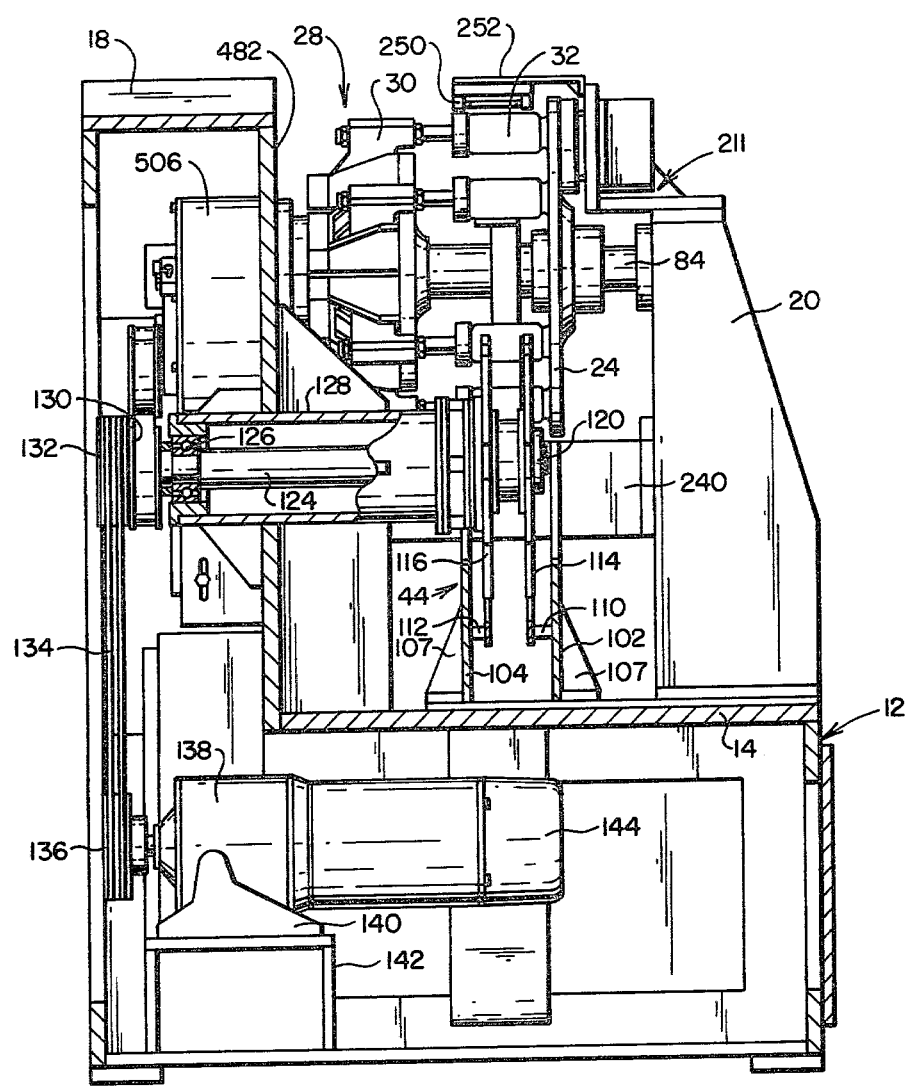
FIG. 5 is a sectional view taken through the plane 5—5 of FIG. 2.
Figure 7:
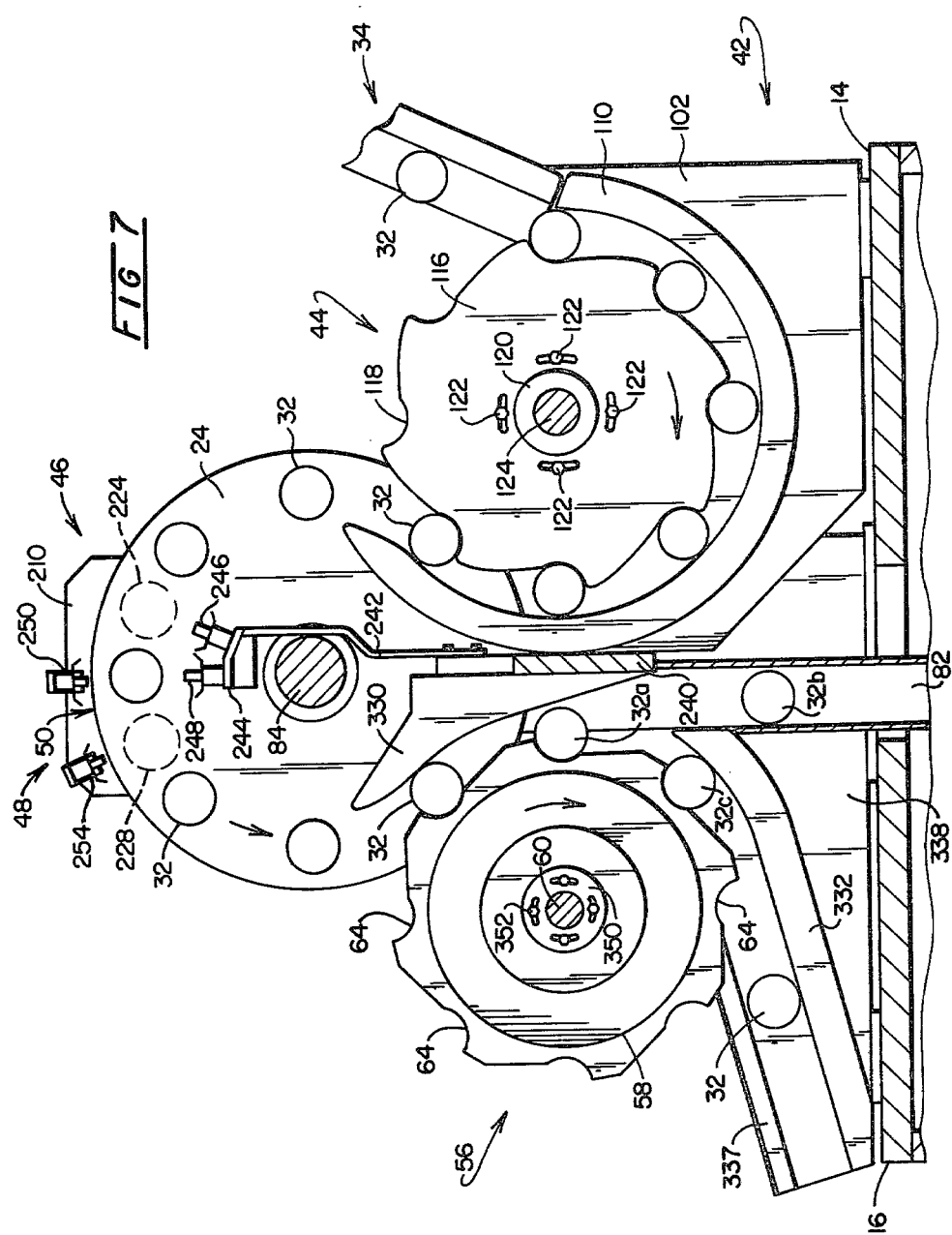
FIG. 7 is a partial sectional view taken through the plane 7—7 of FIG. 3.

As is revealed in FIG. 5, infeed star wheel 44 is formed of two spaced parallel wheels or disks having identically profiled peripheries which are machined to define a sequence of regularly spaced cradles certain of which are revealed at 118 (FIG. 7). Disks 114 and 116 are adjustably mounted upon a hub 120 by slot and bolt assemblies as represented at 122 in FIG. 7. Assemblies 122 permit a rotational phase adjustment of wheel 44. FIG. 5 reveals that the hub 120 is fixedly journaled over a drive shaft 124 which, in turn, is supported by bearing assemblies, one of which is revealed at 126, which are, in turn, supported by a cylindrically shaped bearing support structure 128 which is fixed to and extends through wall 482 of frame portion 18. Drive shaft 124 extends outwardly from bearing 126 at which position it initially is coupled to a timing sheave 130 of a configuration incorporating teeth and suited for operation in conjunction with a timing belt. Outboard of sheave 130 is driven sheave 132 which is driven through a drive belt connection 134 by a drive sheave 136, in turn coupled to the shaft of an electric motor 138. Motor 138 is shown coupled to frame portion 12 by a suitable bracket 140 mounted upon a platform 142. The opposite side of motor 138 is connected to an air brake represented at 144. Pressurized air is supplied to air brake 144 from a source thereof earlier described in connection with FIG. 1 as being directed to preliminary treatment at 54.

As is revealed in FIG. 7, containers 32 are rollably, guidably or slideably directed along chute 34 into engagement with the spaced cradles 118 of infeed star wheel 44 and are retained during the rotational motion thereof as represented by the arrow by cooperation with guide rails 110 and 112. As wheel 44 is rotated, the containers 32 reach a position for reception by the carrier or transfer wheel 24. This point of reception is at about 45° below horizontal as taken through the centerline of centrally disposed shaft 84.

Carrier Wheel and Central Shaft

Figure 6:
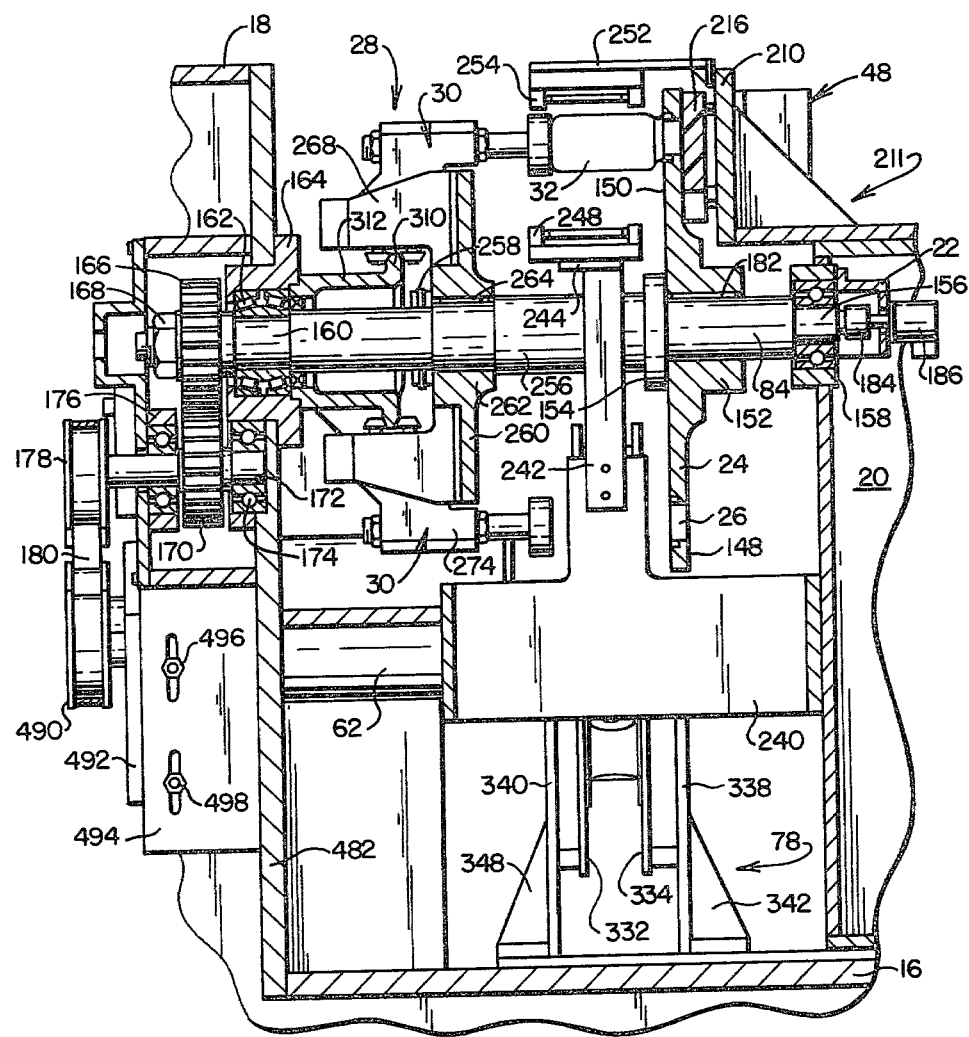
FIG. 6 is a partial sectional view taken through the plane 6—6 of FIG. 2.

Referring to FIGS. 6 and 7, the carrier wheel 24 is shown having a circular periphery through which are positioned a sequence of eight, regularly spaced apertures 26. The spacing of such apertures will correspond to the spacing of cradles positioned within infeed star wheel 44 as well as within the discharge transfer assembly 56. Of course, the number of apertures can be varied to suit the requirements of the designer. With the selection of eight, regularly spaced apertures 26, their mutual spacing will represent an arc of 45° taken through the central axis of wheel 24 which coincides with the central axis of shaft 84. FIG. 6 reveals that transfer wheel 24 is formed having a flat receiving surface 150, an oppositely disposed flat surface 148 and is configured to have an integrally formed hub portion 152. The flat receiving surface 150 of wheel 24 is mounted against an annular flange protrusion 154 formed integrally with shaft 84 and the wheel 24 is fixed to shaft 84 for rotative driven association therewith. FIG. 6 reveals that shaft 84 includes a necked down portion 156 which rides within a bearing assembly 158 fixed, in turn, to pedestal 20.

Looking to the opposite side of shaft 84, note that a bearing surface 160 is formed therein which is journaled for rotation within a double tapered roller bearing 162. Bearing 162, in turn, is mounted within a cam holder 164 which, in turn, is mounted within an aperture formed within wall 482 of frame portion 18. That portion of shaft 84 extending outwardly from bearing 162 is connected to a gear 166 which is fixed thereto by a keying arrangement (not shown) and the entire assembly is retained in appropriate position by a threaded portion and retainer nut arrangement 168. Gear 166 is enmeshed with a second gear 170 which is fixed to a shaft 172 extending between bearing assemblies 174 and 176. Assemblies 174 and 176, in turn, are mounted within frame portion 18 between wall 482 and cover assembly 506. To provide lower noise and to reduce the momentum of revolution of the assembly, preferably, one of the gears 168 or 176 is formed of a lightweight fibrous material, for example, laminated phenolic-linen, NEMA grade "LE" (MIL-P-150 35 Type FBE). Shaft 172 is shown extending outwardly and is fixed to a timing sheave 178 which is shown to be driven by a timing belt 180. For this purpose, timing sheave 178 preferably is formed having teeth suited for enmeshment with the corresponding corrugations of belt 180.

Preferably, carrier wheel 24 is fixed to shaft 84 by a keyway connection represented generally at 182. With the arrangement shown, drive is imparted to sheave 178 from belt 180 which, in turn, ultimately is driven by energization of electric motor 138. Sheave 178 serves to rotate shaft 172 and gear 170, which rotates shaft 84 through its drive relationship with gear 166. Outwardly disposed from bearing assembly 158 is a coupling 184 which extends to a shaft encoder 186. Encoder 186 will be seen to serve the function of evolving a position related clock pulse for the control system associated with apparatus 10.

Figure 9:
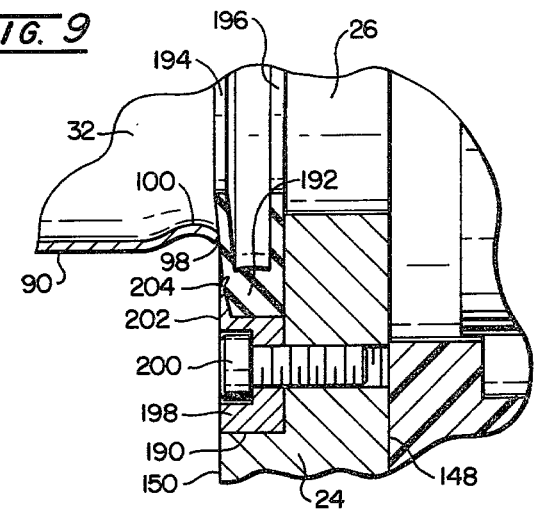
FIG. 9 is an enlarged fragmentary view of a portion of FIG. 8.

Referring additionally to FIGS. 8 and 9, the structure of carrier wheel 24 with respect to the peripheries of each of the apertures 26 is revealed in detail. The aperture openings 26 formed within wheel 24 are provided having a circular inset or counterbore 190 which retains along an inwardly disposed portion thereof with respect to aperture 26 an opaque polymeric flexible seal 192 which is shown having a generally U-shaped cross section. Preferably, seal 192 is formed of black polyurethane, Durometer: 70. The seal is ring-shaped and is formed having a centrally disposed circular opening coaxially disposed with respect to the axis of an associated aperture 26. Adjacent this circular opening, seal 192 defines a contact surface 193 for receiving rim 98. The circular opening within seal 192 is shown defined by peripheries 194 and 196 (See FIG. 9). Seal 192 is retained in position by a retainer ring 198 shown retained in position by machine screws as at 200 spaced in annular fashion about apertures 26 and in threaded engagement with wheel 24. Note, that the heads of the screws 200 are each recessed such that no protrusion extends outwardly from the flat receiving surface 150 of carrier wheel 24. Seals 192 are retained by rings 190 through the utilization of a lip portion 202 integrally formed with the rings and extending outwardly over the adjacent outwardly disposed periphery of seal 192. Note in FIG. 9 that lip or flange 202 extends to a rolled edge 204 which extends inwardly into the polyurethane material forming the seal 192. This configuration of the flange or lip 202 with edge 204 is important to the proper operation of the apparatus at hand. As will be discussed in detail later herein, containers 32 are released to be moved under the dynamics of the apparatus, such that their removal rearwardly from clamping engagement with carrier wheel 24 is one of free movement. Because they will become slightly canted, for example about 7° from their clamped horizontal axial alignment, the rim 98 of a container 32 would otherwise confront and engage the edge 204 of flange 202 and fail to move through the remaining functions of the apparatus. No protrusion of any sort may be permitted to encounter rim 98 as container 32 essentially free-falls away from its engagement with wheel 24. It is this permissible disengagement which, inter alia, permits a reduction in the cost of producing apparatus 10.

Inspection Stations and Light Sources

Figure 10:
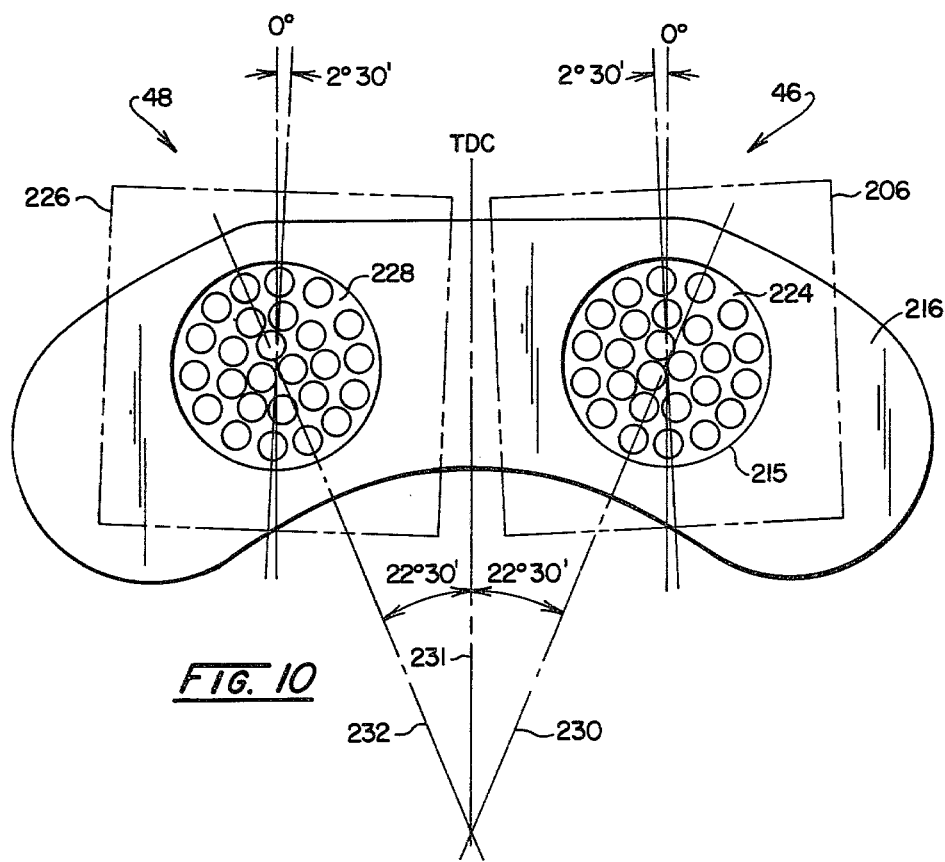
FIG. 10 is a partial sectional view taken through the plane 10—10 in FIG. 8.

Inspection stations 46 and 48 have been described in connection with FIG. 2 as being mounted upon pedestal 20 along the upwardly disposed portion thereof. These inspection stations are aligned with respect to carrier wheel 24 such that apertures 26 will move along a locus into successive alignment with the photocell arrays of the stations. Looking additionally to FIG. 8, the general structure of inspection station 46 (which is substantially identical to station 48) is revealed. Inspection station 46 is shown having a rectangular housing 206 having outwardly depending flanges 208 which are attached to a plate 210 representing the upward portion of a bracket assembly 211 of pedestal 20 and which is positioned in parallel alignment with the flat rearward surface 148 of wheel 24. Housing 206 retains the amplification stages and the like associated with an array of photodiodes positioned within a cylindrical mounting ring 212 and has a cylindrical necked down portion 214 extending outwardly therefrom. This necked down portion 214 is retained within an opqaue polymeric contact member 216 having a periphery extending across both inspection stations 46 and 48 as shown in FIG. 10. Retention of necked down portion 214 within a corresponding aperture 215 within contact member 216 is by an O-ring 218 as well as in consequence of the retention of member 216 in place by the abutting and sliding engagement of its flat forward surface 220 with carrier wheel 24 flat rearward surface 148. Member 216 is continuously urged into this sliding engagement by compression springs associated with each inspection station as revealed at 222. "Nylatron" may be used as the material forming contact member 216. With the arrangement shown, as an aperture 26 approaches inspection station 46, it becomes aligned with the photocell array within mounting ring 212, whereupon defects within an associated container 32 are detectable by virtue of light passing through its structure. Each of the inspection stations 46 and 48 are identically structured but mounted in spaced relationship along the locus of travel of the apertures 26. FIG. 10 reveals this mutual orientation for the stations and their arrays. In the figure, station 46 is shown supporting an array 224 of 26 photodiodes, while the housing 226 of station 48 is shown supporting an identical array 228 of photodiodes. As represented by radii 230–232, arrays 224 and 228 are positioned on radii extending through the axis of main shaft 84 and extending outwardly from radii 231 representing top dead center (TDC) by an angular amount of 22° 30′. Thus, the arrays 224 and 228 are separated by 45° in correspondence with the separation of the adjacent apertures 26 on wheel 24. Note additionally, that array 224 is rotated about its center in the direction of container movement by 2°, 30′, while array 228 is rotated in an opposite direction by an angle of 2° 30′. This adjustment is made in consideration of the orientation of the light sources to be described below.

Referring to FIGS. 6 and 7, the light source arrangement of apparatus 10 is revealed in detail. This lighting arrangement, earlier described in general at region 50, is one which achieves high reliability in testing while minimizing the number of lamps and power required for illumination. In the instant embodiment, two lamps are utilized principally in connection with each inspection station 46 and 48. These lamps have been selected as of a quartz variety rated at 300 watts apiece. FIG. 6 reveals a tie bar 240 extending across the frame and connected between wall 482 and pedestal 20. Connected to tie bar 240 is a bracket 242 having an upwardly disposed mounting assembly 244 upon which are mounted quartz lamps 246 and 248 (FIG. 7). This mounting is such that light emanating from lamp 246 and its associated reflector is directed at a principal angle of $22\frac{1}{2}°$ with respect to vertical extending through the axis of shaft 84. As such, light from the lamp is directed along a radius 230 passing the center of inspection station 46 array 224. Lamp 246 cooperates with an upwardly disposed lamp 250 mounted upon a mounting assembly 252 extending from plate 210 of platform 211. Lamp 250 is aligned with the top dead center radius 231 described along with radius 230 in connection with FIG. 10. With such lighting, as a container 32 approaches array 224 at inspection station 46, its leading sidewall portion 90 principally is illuminated by lamps 246 and 250.

Now, looking to the illumination associated with inspection station 48, note that lamp 248 is aligned so as to illuminate principally directly vertically upward, i.e. in alignment with radius 231. Lamp 248 cooperates with lamp 254 which is supported by mounting assembly 252 in an orientation wherein its principal illumination is directed along a radius corresponding with that shown at 232 in FIG. 10 which is inclined $22\frac{1}{2}°$ from vertical radius 231. With the arrangement shown, as a container 32 approaches inspection station 48 array 228, the illumination impinging upon it as it approaches and passes station 48 is one principally illuminating the lagging portions of its sidewall portion. It may be observed, therefore, that the principal illumination at station 46 is one illuminating from below at an angle of $22\frac{1}{2}°$ from vertical combined with vertical lighting from above, while the opposite condition obtains at station 48 wherein upwardly directed light is along a vertical axis and downwardly directed light emanates from light directed along a radius inclined $22\frac{1}{2}°$ from vertical.

Holder Assembly

The holder components have been generally designated at 28 in the earlier figures. These components function to receive containers 32 from infeed star wheel assembly 44 at a position of about 45° below horizontal as taken through the axis of shaft 84 and, utilizing reciprocative retention components 30, urge cans 32 into properly aligned positions against the seal 192 contact surfaces 193 surrounding as well as defining apertures 26 within carrier wheel 24.

Looking initially to FIG. 6, a clamp wheel 260 is shown having a centrally disposed hub portion extending rearwardly at 262 and journaled over drive shaft 84. FIG. 11 reveals that hub portion 262 is retained in position against an enlarged portion 256 of shaft 84 by a collar 258 pinned to shaft 84 and is formed having surfaces 266 which define an octagon. These surfaces 266 serve to provide accurate seating for slide housings 268 of a sequence of eight reciprocative retention components 30. As further is revealed in FIG. 11, the forward facing surfaces of slide housings 268 are retained within corresponding slots 270 formed within the flat outwardly disposed portions of clamp wheel 260. FIG. 12 shows that the housings 268 further are retained in position by CAP screws (preferably four) as at 272. Slidably retained within each slide housing 268 is a carriage or clamp slide 274 shown in section in FIG. 12. The outwardly disposed portion of each clamp slide 274 is bored to receive and support a rod shaped clamp stem 276 which is adjustably secured thereto by jamb nuts 278 and 280 (FIG. 12). As is revealed in FIGS. 8 and 12, the forward end of each clamp stem 276 is connected to a contact member 282 which is formed of a transparent material such as an acrylic polymer and is retained in place by a button head screw 284. Each contact member 282 has a flat outwardly disposed contact surface 286 within which may be disposed three steel wear pins, one of which is revealed at 288 in FIG. 8 in contact with the bottom protruding edge of container 32. These pins may be retained in place by additional pins at 290. Note in FIG. 8, that no technique of container 32 attachment is present in connection with the structure of contact members 282. Containers 32 are retained against the contact surfaces 193 of carrier wheel 24 by the abuttable contact made by surfaces 286 adjacent their bottom portions. As is apparent, by manipulating nuts 278 and 280, contact members 282 may be adjusted to provide proper positioning for holding containers 32 in place. Where containers of different lengths are contemplated, this manipulation may be made or the clamp stems 276 may be replaced with stems of different length.

Clamp slides 274 are slidably, reciprocably mounted within slide housings 268 in consequence of their connection with slide pins 290, as revealed in connection with FIG. 12. Pin 290 is shown therein to ride within cylindrically shaped bearing surfaces 292 and 294. Connection of pin 290 to clamp slide 274 is by an eccentric stud 296 and fixed stud 298, stud 298 being threadably engaged through assembly 274 into pin 290, while eccentric stud 296 protrudes through the outwardly diposed surface of slide 274 and is retained in place by a nut 300. Stud 298 is coupled to slide pin 290 by threaded engagement therewith. The inwardly extending portions of studs 296 and 298 rotatably receive roll type cam follower assemblies, respectively, at 302 and 304. Follower assembly 302 is retained in place by nut 306, while follower assembly 304 is retained in position by nut 308 (FIG. 12).

Cam follower rolls 302 and 304 ride in positive engagement with the outwardly depending cam profile portion 310 of a bell shaped cam 312. Looking additionally to FIG. 6, cam 312 is shown fixedly journaled into the forward face of cam holder 164 which, in turn, has been described as retaining bearing 162. A seal is shown intermediate bearing 162 and cam 312. With the arrangement, the positioning of cam 312 with respect to shaft 84 is idealized and a cam arrangement of improved smaller radial dimension is made available.

Returning to FIG. 12, it may be observed that cam followed assemblies 302 and 304 are in positive, continuous engagement with cam profile portion 310 and, to assure such positive engagement, the eccentric stud 296 may be rotated at its noncircular upper extremity to urge follower assembly 302 into appropriate positive contact. This positive contact assures the integrity of movement of clamp slide 274. In effect, no "slop" or "slap" is witnessed with the arrangement and a highly desirable very accurate reciprocative movement of each component 30 is achieved. This accuracy is taken advantage of in the technique for releasing containers 32 by permitting the avoidance of a form of yieldable contact between contact surface 286 and the bottom portion of each container 32. When surface 286 is retracted from engagement with the bottom wall portion 92 of a container 32, the movement and separation is well defined to permit the discharge function to perform with considerable simplification and with the avoidance of containing techniques of the prior art such as applying vacuum through contact members 282 and the like.

Figure 13:
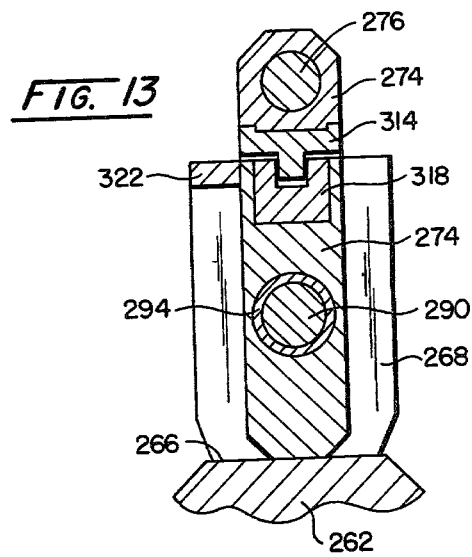
FIG. 13 is a partial sectional view taken through the plane 13—13 in FIG. 12.
Figure 14:
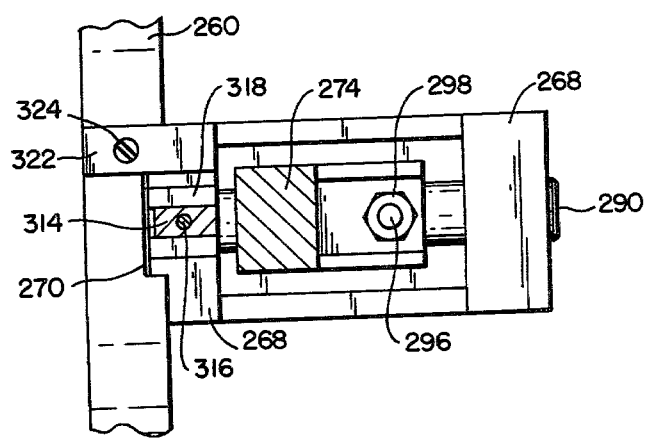
FIG. 14 is a partial sectional view taken through the plane 14—14 in FIG. 12.

Referring to FIGS. 12-14, the radial adjustment features of components 30 are revealed. In the figures, the inwardly disposed portion of clamp slide 274 adjacent clamp stem 276 is shown attached to a key or guide by a flat head machine screw 316 (FIG. 14). The lower portion of guide 314 nests for reciprocal movement within a slide gib 318. Gib 318, in turn, is connected to slide housing 268 by flat head machine screw 320 (FIG. 12). Thus, the radial integrity of the clamp slide 274 is assured, inasmuch as its uppermost portion is secured within the keyway defined by gib 318 within which rides key or guide 314 to assure proper alignment and permitting simplified adjustment during assembly. A keeper 322 (FIGS. 11, 13 and 14) coupled to the outward periphery of clamp wheel 260 by flat head machine screw 324 (FIG. 14) retains the entire assembly in place.

The profile defined by the cam 312 profile portion 310 is one providing for a 4 mm throw in a 16° arc, as represented by an arc defined from its center axis for the typical rotationed speeds encountered, this amounts of an imposition of about 3-4 g forces which, when considered in conjunction with predecessors of the instant apparatus, represents a considerable reduction in the intensity of throw. For example, larger throws of about 10 mm in 12° have been common, representing a dymamic condition of about 36 gs. For the most part, the contacts carried out by the retentive clamping components now substituted by component 282 were of a yieldable nature so as to avoid damage to the containers and to assure a positive vacuum pick-up of the rearward portion of the containers. Note, with the instant apparatus, that the contact is non-yieldable and somewhat gentle in nature.

With the holder arrangement shown, the entire reciprocative retention component assembly 30 may be removed by removing keept screw 324 and the four cap screws 272.

Discharge Assembly

Returning to FIGS. 2, 3 and 7, the discharge components are revealed generally at 56 as including the earlier-described discharge transfer wheel 58 rotating upon a shaft 60 which, in turn, is supported by bearings (not shown) positioned within a support cylinder 62 in a manner similar to the support of shaft 124 within support cylinder 128 (FIG. 5).

FIG. 7 reveals that containers 32 enter the domain of the discharge function 56 at a position about 45 degrees below horizontal, as taken through the center of shaft 84. Release of the containers 32 occurs as contact surface 286 of contact member 282 (FIG. 8) is retracted by an assembly 28. The released container 32 then is free within apparatus 10 but is captured by discharge wheel 58 cooperating with an internal guide rail assembly 330 which is coupled to tie bar 240. The uppermost region of assembly 330 guides containers 32 into the cradle portions 64 of wheel 58. In the event that no defect has been detected in the container, then suction port assemblies 66 (FIG. 3) retain the container as it is carried away from guide assembly 330 as is represented by container 32a in FIG. 7. Where a defect has been detected, however, no such retention of the container is made by port assemblies 66 to retain the container within cradle 64 and the rotational dynamics of the apparatus cause the can to be rejected into discharge chute 82, as depicted by container 32b in FIG. 7. Thus, the containers 32 are contacted and moved into cradle 64 at a receiving position and are retained by vacuum until they reach a discharge position in the vicinity of can 32c as shown in FIG. 7. Containers 32 are retained or controlled, however, by lower disposed spaced guide rails 332 and 334 (FIGS. 3 and 7). Additionally, upwardly disposed rails are provided as needed, one being represented at 336 in FIG. 7. As represented in FIGS. 3 and 6, parallel side guides are provided at 338 and 340 which are mounted upon top plate 16 and which, respectively, serve to support lower guide rails 334 and 332. Brackets 342 and 344 are shown buttressing side guide 338, while a similar bracket arrangement including brackets 346 and 348 is provided to buttress side guide 340 (FIGS. 3 and 6).

FIGS. 3, 7, 15 and 16, reveal that discharge star wheel 58 is mounted upon shaft 60 by a mounting sleeve 350 combined with slot and bolt assemblies 352, the threaded bores within wheel 58 being shown in FIG. 16 at 354. The slot and bolt arrangement 352 permits an adjustment of the rotational phase relationship of wheel 58 with carrier wheel 24. Sleeve 350 is keyed to shaft 60 as represented at 356 in FIGS. 15 and 16. The key at 356 is represented in FIG. 15 as being retained by a set screw 358 extending through sleeve 350.

FIG. 16 reveals that cradles 64 are provided having an arcuate contour, that contour closely approximating the contour of the sidewall portions 90 of containers 32 and represents the positions where vacuum ports 66 are provided as one component of the container retention arrangement of apparatus 10. The port assemblies 66 are formed including multiple counterbores 362 positioned within each cradle 64 and within which are inserted flexible polymeric contact components or cups 364 fashioned, for example, of rubber. Components 364 nest within the bores 362 and are retained in position by centrally bored bolts 366. The centrally disposed bores of bolts 366, one of which is shown at 368 in FIG. 15, communicate with passageways generally designated 360 but present as two arrays, 360a and 360b, as represented in FIG. 16. These passage arrays provide for passage 360 communication to alternate ones of the sequence of cradles 64 about the periphery wheel 58. For example, passages 360a extend to transverse bores 370a extending to the flat outer surface 372 (FIG. 15) of wheel 58. Similarly, transverse bores 370b extend from surface 372 to provide passage communication to corresponding passages 360b. Thus, a first spaced sequence of outlet ports 370a is provided along a circular locus defined by the rotation of wheel 58 and at a given radius from the axis of shaft 60. Additionally, a second spaced sequence of outlet ports in 370b is provided which travel about a circular locus with wheel 58 which is radially inwardly disposed from the locus of movement of ports 370a.

Referring additionally to FIG. 17, additionally mounted over sleeve 350, is a cylindrically shaped vacuum manifold 68 having a first array of transverse bores 374a extending therethrough and aligned in vacuum transmitting communication with corresponding bores 370a within discharge wheel 58. Similarly, transverse bores 374b are provided which are aligned for vacuum transmitting communication with corresponding transverse bores 370b within wheel 58. The inwardly disposed surface 378 of manifold 68 is flat and is retained against corresponding surface 372 of wheel 58 by machine screws (not shown). The opposite, flat face 380 of manifold 68 is provided having shallow, slightly arcuate slots 382a extending from bores 374a and similar slots 382b extending from bores 374b.

Referring to FIGS. 15 and 18-21, a valve assembly, represented generally at 390 is revealed which coopertes with slots 382a and 382b in face 380 of manifold 68. Assembly 390 is mounted upon a bracket 70 (FIG. 3) to which a stationary shaft 392 is attached through a flange portion 394 thereof by machine screws 396. The positioning of stationary shaft 392 is such that it is generally axially aligned with the axis of shaft 60. FIGS. 15 and 19 illustrate a valve clamp 398 which is positioned over stationary shaft 392 and tightened thereagainst by bolts as at 400. Clamp 400, in turn, is coupled to a valve bracket 402 by machine screws 404 and 406. The upper and lower disposed edges of bracket 402 are connected as by machine screws 408 (FIG. 21) to respective support plates 410 and 412 which extend outwardly therefrom. Plates 410 and 412, in turn, respectively support solenoids 72 and 74.

Bracket 402 has a generally U-shape configuration such that a generally rectangular opening 414 is formed therein which serves to retain valve components. Looking to FIGS. 18, 20 and 21, a rectangular valve contact plate 416 having spaced arcuate shallow slots 418a and 418b formed therein along its flat outwardly disposed face 420 is revealed. Plate component 416 nests slidably within opening 414 of valve bracket 402. Slots 418a and 418b are positioned to communicate with respective slot groups 382a and 382b formed within face 380 of manifold 68. Contact plate 416 is formed of a polymeric material to achieve movable, sealing contact with manifold 68 and, additionally, is configured having an inwardly disposed rectangular slot or opening 422 the cross section of which is revealed in FIG. 20. As shown in FIG. 18, bores 424 and 426 are formed through component 416 from within slot 418a, while spaced bores 428 and 430 are provided extending through slot 418b. These bores communicate with corresponding passages or bores within a valve plate 432 positioned within slot 422 of component 416. The latter bores, as shown at 424a, 426a, 428a and 430a in FIG. 21A form a continuation of bores 424, 426, 428 and 430 and extend to respective, shallow, thin slots as at 424b, 426b, 428b and 430b (FIG. 21A) at the upward surface 436 thereof. The latter slots cooperate with corresponding slots, for example as shown respectively at 438 and 440, formed within adjacent slidable, shuttle-like, valve members identified respectively at 442 and 444.

Looking to FIGS. 19 and 21, slide members 442 and 444 are retained in position by valve guides 446 and 448 which are attached to valve bracket 402 by machine screws 450-453. As represented in FIG. 21, valve guides 446 and 448 are configured incorporating a biasing arrangement including springs as at 454 and 456 which cooperate with spring pads shown, respectively, at 458 and 460. These biasing assemblages urge slide members 442 and 444 into contact with valve plate 432, as well as serve to urge valve contact component 416 into engagement with face 380 of manifold component 68 (FIG. 15). FIGS. 19 and 20 reveal that slide member 442 is attached to the plunger 462 of solenoid 72 by the insertion of a flange formed upon the latter within an opening 464 formed within one end of the slide member. Similarly, a flange shaped tip of the plunger 466 of solenoid 74 is configured to nest within an open slot opening 468 within slide member 444.

Plungers 462 and 466 are spring biased outwardly to a normal or neutral position and are retracted upon the energization of the windings within respective solenoids 72 and 74. When the windings of the solenoids are not energized, a vacuum conduit connection as at 470 with respect to slide member 442 and 472 with respect to slide member 444 will provide a corresponding vaccum connection with respective conduits 424 and 430 of valve contact component 416 (FIG. 18) by the alignment of conduits extending thereto through plate 432 and the earlier-described slots associated therewith. FIG. 21 shows one such alignment with respect to slide member 442, connector 470 being shown aligned through bore 474 and slot 438 with corresponding slot 424b formed within plate 432. From slot 424b, communication then is made to bore 424 and slot 418a in component 416. However, upon energization of the winding of solenoid 72, slide member 442 will be moved toward solenoid 72 as plunger 462 retracts to an extent permitting slot 440 to be aligned with slot 426b (FIG. 21). A bore 476 is formed within slide member 442 to communicate with slot 440 such that bore 430 communicating with slot 418b is open to the atmosphere a condition which serves to negate any retention of a container 32 sidewall by an appropriate vaccum port assembly 66 in discharge wheel 58. Solenoid 74 operates in similar fashion in connection with slide member 444, a bore 478 communicating with the atmosphere and ultimately being aligned with conduit 424 within valve contact component 416 and, consequently, slot 418a when the winding of solenoid 74 is energized. Conversely, vacuum input 472 to member 444 is communicated with bore 426 and slot 418a when solenoid 74 is in a normal condition, its winding being unenergized.

As is apparent, two separate retention circuits are provided with the discharge configuration, so as to accommodate for any lag necessarily involved in the actuation of solenoids 72 and 74, as well as in the development of an appropriate vacuum. Valve bracket 402 is rotationally adjustable about stationary shaft 392 through clamp 398 such that the receiving position at which a container 32 is retained by vacuum and the discharge position at which point slots 382a or 382b are released from engagement with face 420 of valve contact component 416 may be accurately established. The design of the vacuum system, while simple, also incorporates practical aspects. For example, when either the winding of solenoid 72 or 74 is energized, the vacuum at respective vacuum inputs 470 and 742 is protected by virtue of the closure of the slots associated therewith against the surface of valve plate 432. During normal, unactuated conditions of the discharge arrangement, the vacuum will be available only within the passages extending to a vacuum port 66 retaining a container 32, the exception to this being the automatic rejection of a container having a deformed sidewall 90 such that coupling thereof with vacuum port assembly 66 is not effected.

Figure 4:
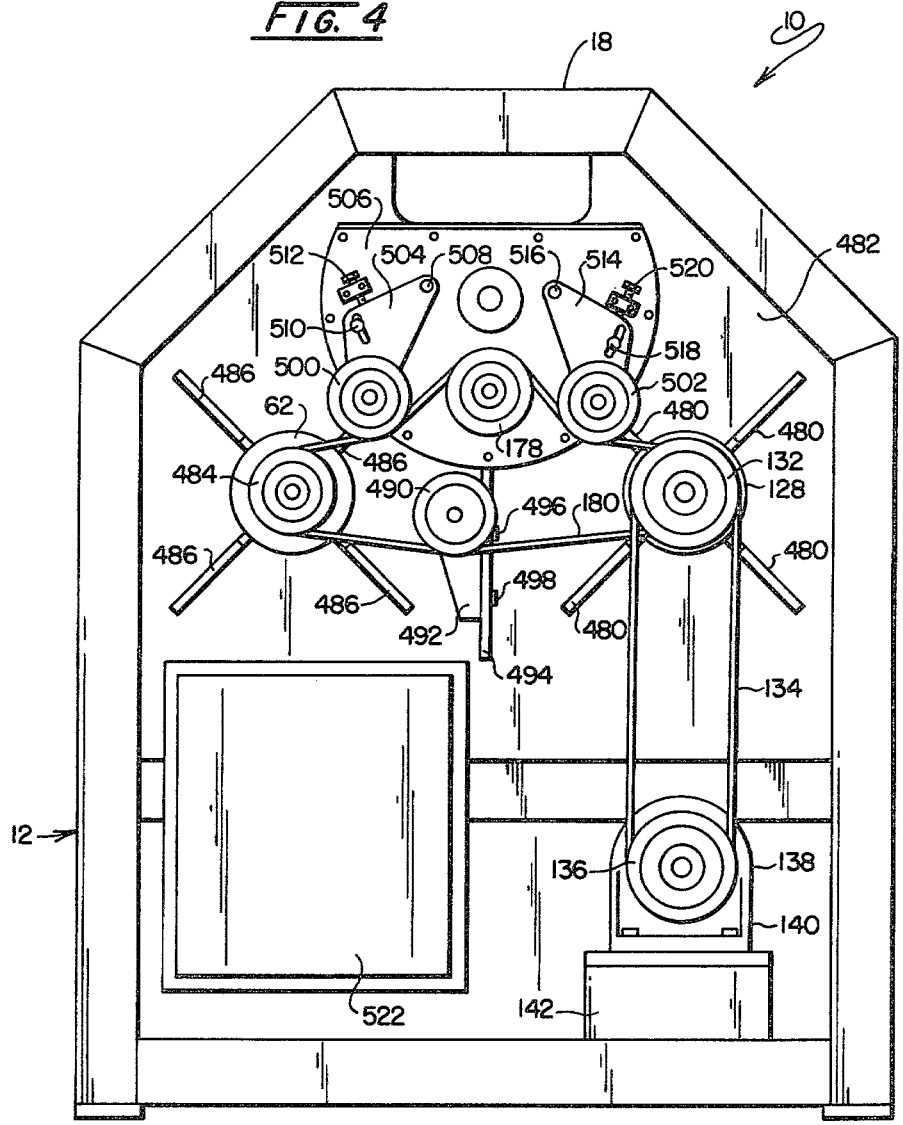
FIG. 4 is a left side elevational view of the apparatus of FIG. 1.

Drive to shaft 60, ultimately, is derived from motor 138, as is described in connection with FIG. 4.

Drive Components

Looking to FIG. 4, the drive output of motor 138 described in connection with FIG. 5 is revealed. Note, that drive sheave 136 coupled with the output shaft of motor 138 is, in turn, coupled by dual belts to a driven sheave 132 which is coupled to the outward tip portion of shaft 124, extending from bearing support structure 128 of the infeed components of apparatus 10. Cylindrical support 128 is shown in FIG. 4 as being supported by triangular shaped buttresses 480 welded to upstanding wall member 482. FIG. 5 shows that, immediately behind driven sheave 132, is a timing sheave 130 over which is positioned a timing belt 180. Belt 180 extends to a timing sheave 178, described in connection with FIG. 6 as being coupled through gears 176 and 166 to central drive shaft 84. From timing sheave 178, timing belt 180 extends over timing sheave 484 which is coupled to shaft 60 extending from the rearward extent of support cylinder 62. Cylinder 62 extends through and is supported by wall 482 as well as by triangular-shaped buttresses 486.

Timing belt 180 is adjusted by a series of idler pulleys including that shown at 490 which is attached by bracket 492 to an outwardly disposed plate 494. As shown in FIG. 6, attachments of bracket 492 to plate 494 is made adjustable by slot and bolt assemblies 496 and 498. Additional adjustment of timing belt 180 is made by idler pulleys 500 and 502 which are positioned on either side of timing sheave 178. Pulley 500 is connected to a support bracket 504 which is connected to the faceplate assembly 506 at a pivot connection by a bolt 508 and through a slot and bolt coupling 510. Accurate positioning of bracket 504 can be provided by manipulation of an adjustment bolt assembly 512.

Similarly, Idler pulley 502 is connected to a support bracket 514 which is pivotally connected to the faceplate of assembly 506 at bolt 516 and bolt and slot assembly 518. As before, accurate adjustment of the position of pulley 502 can be carried out by manipulation of an adjustment bolt assembly 520.

With the arrangement shown, a drive system as well as the principal components of apparatus 10 provide utilizing members of relatively low mass which permits rapid and improved braking utilizing air brake 144 in the event of a malfunction. The relative rotational phase between input shaft 124 and central shaft 84 as well between the latter and discharge shaft 60 may be adjusted by relative movements of idler pulleys 500 and 502. FIG. 4 also reveals the presence of a door 522 of a box for enclosing electrical input components.

Control System

The control system of the apparatus 10 serves to respond to output signals generated by the photosensitive arrays 224 and 228 and then treat these signals (derived from two stations) such that an appropriate composite defect signal is generated which may be utilized to selectively energize an appropriate one of the windings of solenoids 72 and 74. Note, that these solenoid windings are energized only in the presence of a composite signal generated in appropriate timed sequence, such that the retention operation of the discharge system 56 is one which normally, mechanically takes place. As noted earlier herein, arrays 224 and 228 comprise a plurality of photosensitive devices such as photodiodes. These photodiodes are interconnected with amplification stages such that the output from each array may be considered as a unitary output signal.

Figure 22:
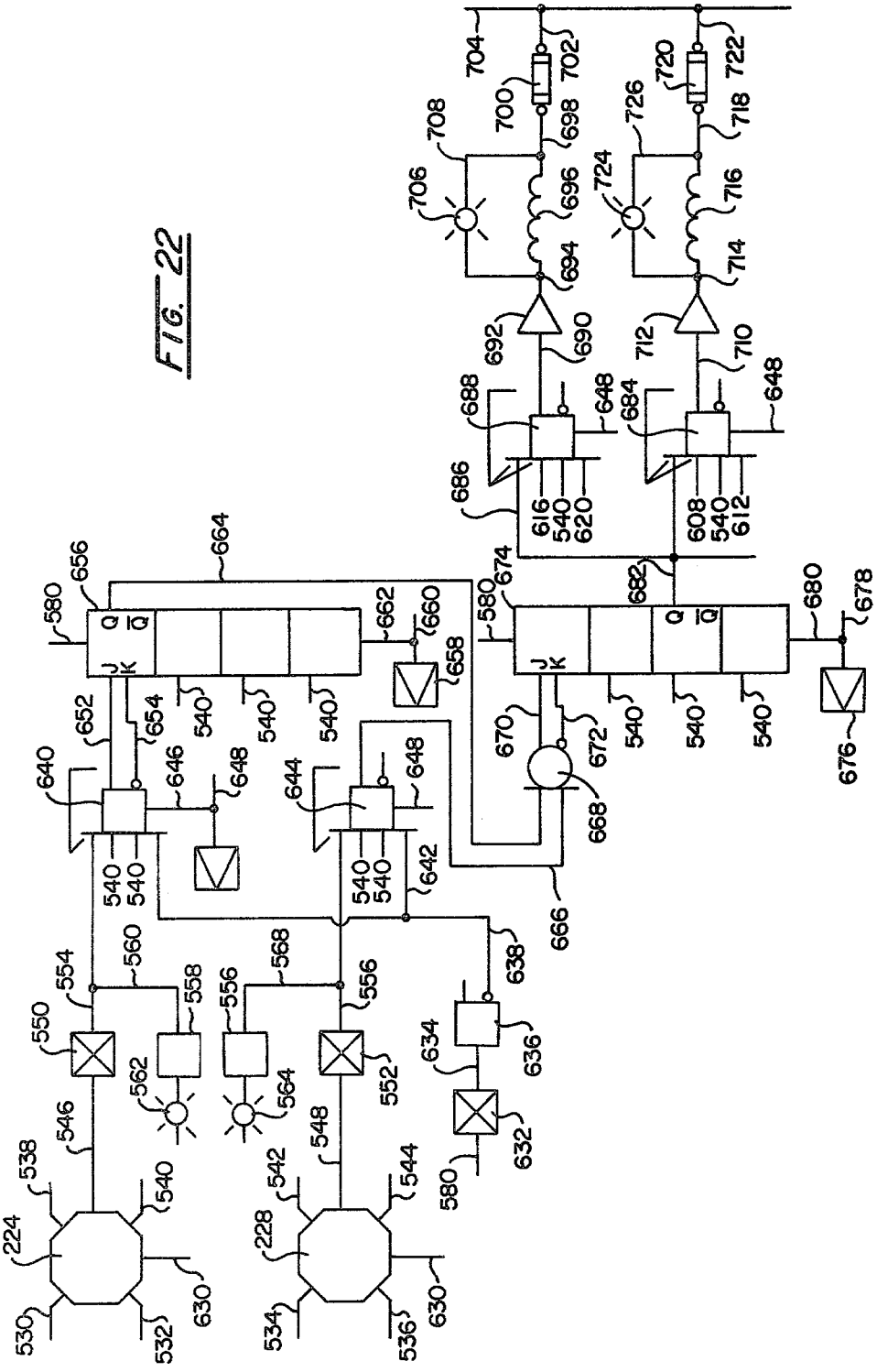
FIG. 22 is a schematic representation of control circuitry of the instant invention.

Referring to FIG. 22, arrays 224 and 228 again are reproduced in symbolic fashion, array 224 being connected through lines 530 and 532 to a conventional d.c. power supply, for example 24 v. d.c., and array 228 similarly being coupled to a similar power supply through lines 534 and 536. Inasmuch as the general circuitry to be described operates within a 15 volt range, arrays 224 and 228 additionally contain optical couplers to transfer their outputs to a 15 volt system and the 15 volt inputs thereto for deriving a correspondingly scaled output signal are shown at lines 538 and 540 for array 224 and at lines 542 and 544 at array 228. The thus treated output signal for array 224 is presented along line 546 and along line 548 for array 228. Logic components preferred for use with the circuit of the instant control system are marketed by Allen-Bradley, Milwaukee, Wisconsin 53204. Such circuits, as noted above, utilize a 15 volt power supply, in conjunction with components having a 7.5 volt nominal switching threshold. This provides a relatively large noise margin which is to be desired in connection with large mechanical devices as are now at hand. The output of each of the arrays at lines 546 and 548 in the presence of no detected defect will be a consistent 15 volt level. However, with the detection of a defect, a pulse will be developed at an appropriate one of the output lines 546 or 548 which will drop to about a 0 point level for the length of the defect detection. The detected pulse outputs then are inverted as at inverter 550 in conjunction with output line 546 and at inverter 552 in conjunction with line 548. Thus the output signal representing a defect at lines 554 and 560 is a positive going pulse. Connected to line 554 is an energizing circuit 558 which responds to a defective container signal through line 560 to illuminate a visible indicia such as a lamp, represented at 562, to apprise the operator of the presence of a container defect. This lamp, for example, may be mounted in console 52 (FIG. 1). Similarly, a console 52 mounted lamp 564 controlled by energizing circuit 566 is provided to respond to a defect output signal at line 556 through line 568. Generally, the output signals at lines 554 and 556 will, as a miniumum, have a duration of about 10 ms, which is sufficient for visual perception and affords the operator an opportunity to monitor the operation of apparatus 10 while working in the vicinity of console 52, i.e. it represents a helpful trouble shooting device.

Figure 23:
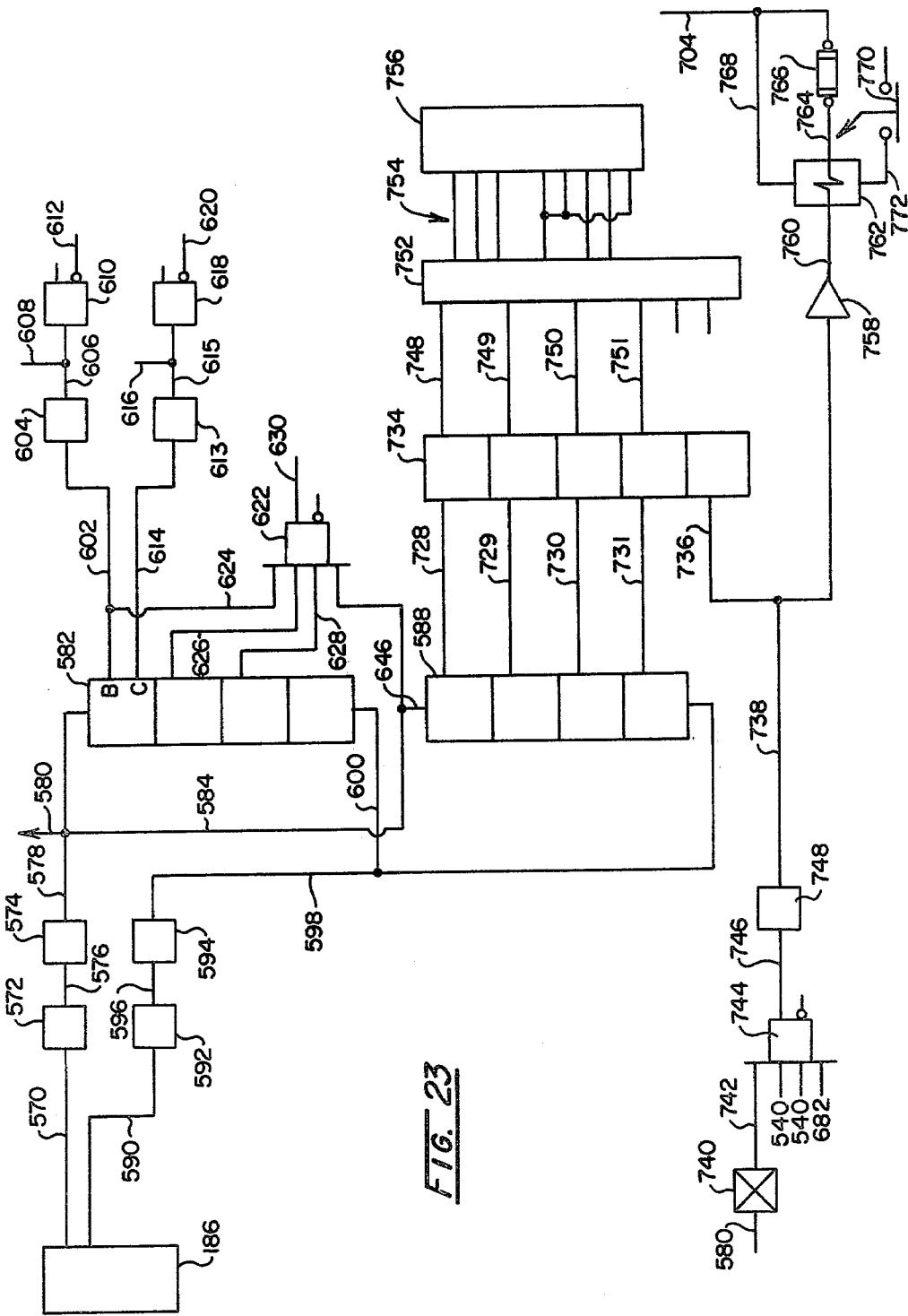
FIG. 23 is a schematic view of other portions of control circuitry utilized with the instant invention.

Turning momentarily to FIG. 23, the encoder described earlier herein as providing output logic related to the rotation of shaft 84 is represented by the same numeration 186. This encoder may be a shaft encoder marketed under the trade designation "Rotaswitch" by Disc Instruments, Inc., Costa Mesa, California, Model 701FS-8-ISLP±15 v. In addition to conventional power inputs, encoder 186 provides an output clock pulse when shaft 84 rotates such that the centerline of a given aperture 26 is aligned with the earlier described radius 231 (FIG. 10) representing top dead center (TDC). Looking to FIG. 25, this position is represented schematically. Additionally, the schematic diagram shows a series of apertures 26 on carrier wheel 24, each such aperture being given a station number (1-8) and the carrier wheel 24 being considered to rotate, for illustrative purposes, in the clockwise direction represented by the arrow. Encoder 186 provides a clock output pulse at line 570 each time the center of one of the eight stations passes radial position 231. Thus, position 231 may be considered a reference position. If further should be noted that the distance between the center of each successive station 1-8 is equivalent to the distance between the center of arrays 224 and 228.

Returning to FIG. 23, the encoder output line 570 is treated for noise avoidance including a delay (100 microseconds) at input squaring function (ISC) 572 and is passed through a driver 574 from along line 576. The resultant output at line 578 is a clock pulse which is directed to several functions as represented in the figures by numeral 580. Note in FIG. 24, the clock pulses are represented in timing diagrammatical fashion.

Line 578 further leads to the input of a decade counter 582 and, through lines 584 and 586 to a second decade counter 588. Counters 582 and 588 may be of the type described at catalogue No. 1720-L710 (Series C) by Allen-Bradley, Inc. (supra).

Figure 24:
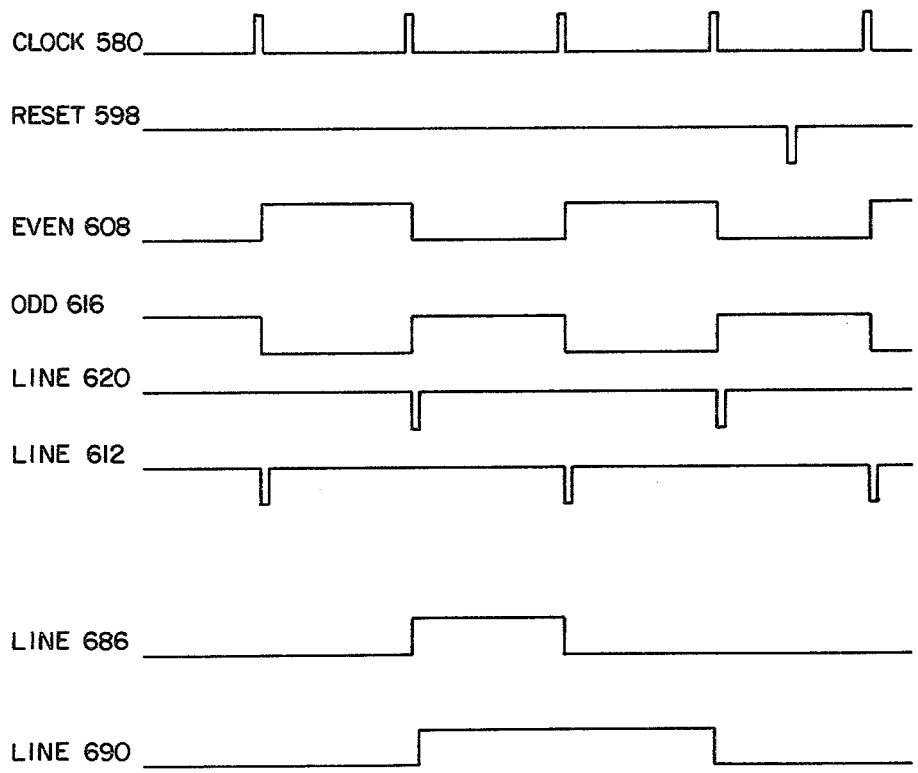
FIG. 24 is a timing diagram associated with the circuitry of FIGS. 22 and 23.

A second output of encoder 186 is provided at line 590 which is treated, as before, by noise limiting components such as ISC 592 and driver 594 connected to the former through line 596. The output of driver 594 is present at line 598 and is directed to the reset input of decade counter 588, as well as through line 600 to the reset input of counter 582. The signal at line 590, as treated at networks 592 and 594, is a pulse representing one complete revolution of carrier wheel 24 or shaft 84. Thus, the pulse at line 598, as represented in FIG. 24, represents a reset pulse.

Figure 25:
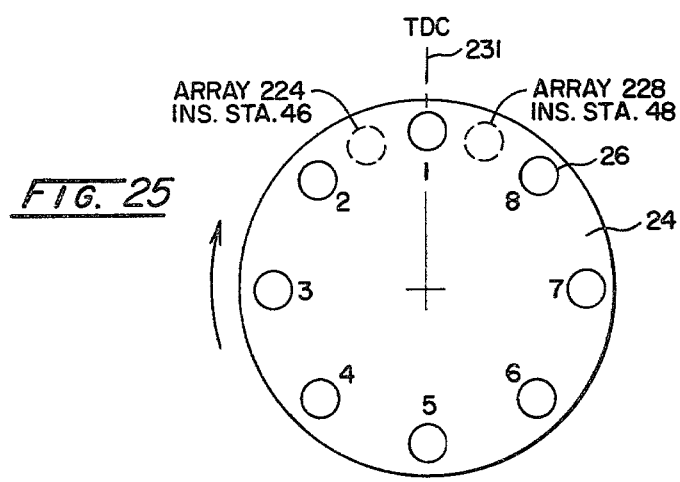
FIG. 25 is a schematic representation of the station orientation of carrier wheel 24 of the apparatus of the invention.

Counter 582 serves, utilizing a developed binary output, to monitor the position of the 0-8 stations described in connection with the schematic portrayal at FIG. 25 as those stations pass the reference position represented by radius 231. Accordingly, the initial stage output of decade counter 582 is present at line 602, whereupon it is passed through an inverter 604 to, in turn, be presented at line 606, which is tapped at line 608. Line 606 is introduced to the input of a pulse shortener or "singleshot" 610 having an output at line 612. Singleshot components as at 610 may be of a variety identified as catalogue No. 1720-L470 by Allen-Bradley (supra) and are used to shorten the pulse width of an input signal and, alternately, can be used to obtain a predetermined propagation delay.

The output at line 608 will be seen to be utilized, inter alia, for the purpose of identifying which of the stations 1-8 (FIG. 25) are odd and which are even so as to evolve a logic for actuating an appropriate one of the solenoids 72 or 74 to achieve alternate reject control through the discharge function.

A second binary output of counter 582 is derived along line 614 which, as before, is directed through an inverter 613 and line 615 to output line 616 and singleshot network 618. The output of the latter network is present at line 620. See FIG. 24 for a timing schematic portrayal of the signals at lines 608, 616 and 612.

The third output of decade counter 582 represents the count 7 transition and is developed at AND gate 622, the inputs to which are derived from line 624 which is coupled to line 602, line 626, line 628 and line 584 which carries the clock pulse. A resultant output at line 630 is returned to photodiode arrays 224 and 228 (FIG. 22) and is used to reset these arrays at the commencement of each revolution of transfer wheel 24 so that they may be continually updated or compensated for thermal and related conditions extant within apparatus 10.

Returning to FIG. 22, the clock pulse developed at line 580 is introduced through an inverter stage 632, thence along line 634 to a singleshot network 636 as above described which has a pulse shortening function and provides an output representing a treated clock pulse at line 638. Line 638 leads to one input of a multiple input sealed AND gate 640 as well as through line 642 to a corresponding input of a similar sealed AND gate 644. Gates 640 and 644 may be of a type identified as catalogue No. 1720-L014 by Allen-Bradley (supra) and serve to provide a retention function at the sealed inputs thereof which permits their use in inserting defect signals to a later memory or shift register function. In this regard, note that gate 640 receives clock information from line 638 and an output signal from array 224 from along line 554. The gate is coupled through lines 646 and 648 to an initial reset component 650 which is utilized to provide a logic 0 output upon initial application of power or after a power interruption. Such initial reset components are available, for example, as catalogue Nos. 1720-L905, L906 (Series C) by Allen-Bradley (supra).

The output of AND gate 640 represents a defect signal synchronized with the clock pulse and developed from the first inspection station incorporating array 224. This output, present at lines 652 and 654, is introduced to the first zone of a shift register 656. Shift register 656 may be present as a four zone shift register marketed as catalogue No. 1720-L811 (Series C) by Allen-Bradley (supra). The clock pulse of the system from line 580 is applied to the clock input of register 656, while an initial reset network 658 is coupled thereto through lines 660 and 662. In general, shift registers consist of cascaded J-K flip-flop memories coupled such that a shift signal (clock pulse) applied to the clock inputs thereof will cause each J-K memory to assume the condition of the previous J-K memory just prior to the shift signal. In the present instance, a logic 1 to logic 0 clock pulse transition applied at the clock input 580 will forward shift all zones of the register. Recalling from FIG. 25 that a clock pulse corresponds to a timed representation of the movement of from one station to a next past reference position 231, the output of the first zone of register 256 will correspond to such movement and is present at line 664. Recall also, that such a single clock spacing represents the elapsed travel time of a given aperture 26 or station (1-8) from inspection station 46 to inspection station 48.

Array 228, representing the second to be encountered inspection station 48 ultimately asserts its output signal along line 556 to sealed AND gate 644 in similar fashion as array 224 asserts its output signal to gate 640. Gate 644 additionally receives a clock input from along line 642 to develop a defect signal at its output lines 666. Line 666 is directed to one input of an OR gate 668, the other input to which is developed from line 664 emanating from shift register 656. OR function 668 may, for example, be of a type identified as catalogue Nos. 1720-L202, L204 (Series C.) by Allen-Bradley (supra). The output of OR function 668 is present at lines 670 and 672 and is introduced to the J-K inputs of a second 4-zone shift register 674. Structured identically as register 656, register 674 receives clock impulses at its clock input through line 580 and is coupled to an initial reset network 676 through lines 678 and 680. The OR function input at 668 to shift register 674 represents either the detection of a defect at inspection station 46 or a defect detection at the second inspection station 48 spaced from the former. Returning momentarily to FIG. 25, it may be observed that it is desirable for carrier wheel 24 and associated holder components to discharge a container somewhere below a radius representing a position 45° below horizontal as taken through the axis of shaft 84. This is the point at which discharge wheel 58 will have accepted a container 32 but not have retained it through its vacuum port assembly 66 associated therewith. Accordingly, shortly after such acceptance, the logic developed from the control system will selectively energize a solenoid 72 or 74 depending upon the odd or even designation of an aperture 26 station. Thus, a count timing is evolved wherein shift register 674 is tapped at its third zone at line 682 to represent the position x, shown in FIG. 25 corresponding with a position just below discharge wheel 58 container 32 reception. Line 682, thus carries a composite defect signal in time synchronism correspondence with the distance between the second inspection station 48 and the position, x, related to the discharge wheel 58 reception position, which is asserted at one sealed input of sealed AND gate 684 and to a corresponding sealed input through line 686 to sealed AND gate 688. See the signal representation for the signal present at line 686 in FIG. 24.

In addition to a conventional power input at line 540, AND gate 688 receives the composite defect signal from line 686 as well as an odd-even carrier wheel 24 station 1-8 designation from lines 616 and 620. Thus, a coordinated defect output is developed at line 690 at a sequentially coordinated point in time. The output at line 690 is represented in FIG. 24, the expansion of the pulse providing for adequate solenoid winding actuation as developed at singleshot output 620.

Line 690 extends through an interface network having a d.c. output function 692 which may be provided as a catalogue No. 1720-B1514 by Allen-Bradly (supra). This device has a low output at line 694 in the presence of a signal at line 690. Line 694 is coupled to the winding of an actuating solenoid as at 72 or 74 selected for odd or even station association. This winding is represented at 690. The opposite side of winding 696 extends through line 698, fuse 700 and line 702 to a power bus 704. This bus, for example, may supply 24 volts d.c. for winding 696 and, with line 694 having a logic low value, winding 696 is energized. An indicator lamp 706 is shown positioned within line 708 extending across winding 696 and provided for purposes of affording a visible indicia of solenoid actuation.

Sealed AND gate 684 also receives the composite defect signal from line 682 in addition to odd-even counter information from lines 612 and 608. In consequence, an even designation of station 18 selection is combined with the composite defect signal and outputed at line 710. Line 710 extends to interface device 712 which is identical to interface device 692 and which has a low output at lines 714 in the presence of a defective container signal at line 710. Line 714 is coupled to the winding of a selected second solenoid 72 or 74 and designated at 716. The opposite end of winding 716 is coupled through line 718, fuse 720 and line 722 to power bus 704 in the same manner as winding 696. Additionally, an indicator lamp 724 within line 726 provides visible indicia that winding 716 is energized.

Two additional functions may be provided by the control system of the invention, one providing a digital readout identifying that station 1-8 at which a defective container has been detected and the other providing a cumulative total of the number of defective containers which have been detected. Returning to FIG. 23, decade counter 588 is represented as receiving a clock input from line 586 as well as a reset input representing one complete revolution of 8 stations through line 598. The binary output of counter 588 is presented at lines 728-731 and is introduced to a display driver 734. This driver 734 may be a type marketed as catalogue No. 1720-L1010 (Series C) by Allen-Bradley (supra). Driver 734 also receives a signal through lines 736 and 738 which represents a clock coordinated composite defect signal. This signal is derived from clock input line 580 which is directed to an inverter 740, thence along line 742 to one input of AND gate 744. The additional logic input to gate 744 is derived from line 682 which represents the composite defect signal derived from shift register 674. The resultant output of gate 744 at line 746 is expanded at adjustable singleshot 748. Pulse stretcher function 748 output is provided through lines 738 and 736 to actuate driver 734, and thus, present station position information of a defect detection through the array of lines 748-751 and interfacing terminal function 752 for presentation through a line array designated generally at 754 to visual digital readout display 756 (Allen-Bradley catalogue No. 1720-L28).

The expanded pulse at line 736 representing the occurrence of a detected defective container 32, is presented through an interface network 758 identical to those described at 692 and 712 in FIG. 22 and a resultant low output is presented at line 760 to the control winding of a mechanical counter represented schematically at 762. Counter 762 is shown having its principal power input at line 764 extending through fuse 766 to power bus 704, as well as a second control line extending from the latter power bus and represented at 768. A reset switch 770 is shown functionally associated with counter 762 through line 772. With the arrangement, counter 762 provides the operator a cumulative totaling of detected defective containers 32 for a given production run.

Operation

Referring to FIG. 1, containers 32 are shown being introduced to the infeed function of apparatus 10 including infeed star wheel 44. As is represented in FIGS. 2 and 7, infeed star wheel 44 cooperates with guide rails as at 110 as well as side guides 102 and 104 to position containers 32 at a location wherein they may be received and retained by the holder arrangement of the invention. As described in connection with FIGS. 6, 11 and 12, this holding arrangement includes eight reciprocative retention components which are rotated by central shaft 84 into positions wherein the contact surfaces 286 of contact components 282 are urged forwardly into contact with the bottom portions 92 of containers 32 (FIG. 8) to urge the rim portions 98 thereof into contact with contact surfaces 193 positioned about apertures 26 formed within carrier wheel 24. Carrier wheel 24 and the holding arrangement 28 rotate in synchronism by virtue of their common connection with shaft 84. The abutting engagement of contact members 282 is one which may be considered somewhat gentle, taking place as about a 4 mm throw in 16 degrees of shaft 84 rotation. This same arrangement is used for the release of contact members 282 from their abuttable engagement with container rearward portions 92. The reciprocative retention components as at 30 are structured such that they are easily demountable from their associated clamp wheel 260 and are positively driven from cam profile defining portion 310 of cam 312. The latter cam is structured in conjunction with cam holder 164 so as to assure the axial alignment of all components and to enhance the rigidity of the holder assembly. Positive drive is provided from cam follower roller assemblies 302 and 304 which are readily adjustable into positive engagement with flange profile portion 308. As carrier wheel 24 rotates from the position of receiving containers 32 and carries out abuttable retention thereof, the interior cavities 94 of the containers 32 are moved (in alignment with apertures 26) across two successive inspection stations 46 and 48. These stations are spaced a distance apart corresponding with the distance between the container 32 positioning stations 1-8 represented by the regularly spaced sequence of apertures 26. In the event a defect is detected by the array of photosensitive devices 224 at inspection station 446, an output signal is developed which is synchronized with a clock signal developed from a reference point corresponding with top dead center radius 231 of the axis of shaft 84. This information is submitted to an AND function and, thence to a sequential memory present as a the first zone of a shift register.

The light source utilized in conjunction with the scrutiny of defects at inspection station 46 has been described in conjunction with FIG. 7, a quartz lamp 246 being positioned along a radius positioned $22\frac{1}{2}°$ from TDC radius 231 and a lamp 250 positioned at radius 231. With such illumination, the leading edge of containers 32 are principally illuminated as they pass array 224. As the containers then are moved toward inspection station 48, the array 228 therein detects defects, if present, and develops a second output signal which is submitted to another ANDing function, thence to an OR function along with the output of the initial shift register to a second shift register arrangement. Illumination of containers 32 as they pass inspection station 48 is one principally illuminating the lagging portions thereof as from lamp 248 positioned at TDC radius 231 and from lamp 254 positioned $22\frac{1}{2}°$ from TDC radius 231 or along axis 232.

The shift register arrangement combined with OR logic, is selected with respect to vertical reference and reception positions such that at a predetermined reception position for the discharge wheel 58, the container 32 will have been released by contact component 282 for movement away from contact surface 193 of seal 192 at each aperture 26. Retainer rings 198 retaining these seals 192 in position are specifically formed having lip portions 202 which are rolled inwardly at their outer edges 204 to permit containers 32 to fall from engagement therewith without encountering an engagement of their outer rims 98 with the retainer rings 198. Containers 32 move rearwardly due to the dynamics of apparatus 10, the principal rearward vector of ths movement being evolved by the heavier weight of their rearward portions 92 as compared with their sidewall portions 90. As a consequence of this arrangement, no retention techniques, for instance utilizing vacuum ports in connection with contact members 282 and the like, are required and the apparatus 10 represents a considerable simplification over devices heretofore available.

The discharge wheel 58, upon receiving containers 34 within its cradle 64 at a position of about 45° below horizontal through the axis of shaft 84 normally asserts a vacuum through vacuum port assemblies 66 upon the container 32 sidewalls 90. This retention continues until the containers 32 are moved to a discharge position whereupon they are diverted into a discharge chute. Those containers 32 having defective sidewalls will not be accepted by the vacuum retention technique and will be discharged through a discharge chute.

Appropriate vacuum valving is provided which is responsive to control system composite defect signals which negates the normal development of vacuum passages leading to vacuum port assemblies 66 such that a defective container 32 is never retained by discharge wheel 58. To improve the responsiveness of the discharge function, two arrays of vacuum passages are utilized in conjunction with two actuating arrangements including solenoids 72 and 74. The control circuitry of the apparatus is similarly structured so as to assign certain of the arrays even numbers of cradles 64 and others to odd designated cradles 64.

Since certain changes may be made in the above-described system, apparatus and method without departing from the scope of the invention herein involved, it is intended that all matter contained in the description thereof or shown in the accompanying drawings shall be interpreted as illustrative and not in a limiting sense.

We claim:
1. Apparatus for automatically testing open-ended containers having an opening surmounted by a rim, a sidewall portion extending to a bottom portion disposed opposite said rim, said apparatus inspecting said containers for the presence of defects in the form of openings in their structure, and comprising:
   means defining a supportive frame;
   a first shaft rotatably supported upon said frame and having an axis of rotation;
   carrier means fixed to and rotatable with said first shaft, having a plurality of apertures therein regu- larly spaced about the periphery thereof and configured in correspondence with the configuration of said container rim for selectively receiving said containers in abutting relationship at contact surfaces thereof;

holder means including a plurality of reciprocative retention components corresponding in number with the number of said apertures, mounted for rotation with said first shaft at locations spaced from and disposed opposite a corresponding said aperture, each said retention component including a contact member extensible into abutting engagement with a said container bottom portion to compressibly urge the rim thereof into light-tight abutting engagement with said carrier means contact surface, and retractable from said abutting engagement to effect a release from said container;

first inspection station means mounted upon said frame adjacent to, stationary with respect to, and in light-tight communication with said rotatable transfer means and including a first photoresponsive device located for successive alignment with each said aperture and said container opening associated therewith for deriving a first output signal upon exposure to light passing through said container defects;

second inspection station means spaced from said first inspection station means, mounted upon said frame adjacent to, stationary with respect to and in light-tight communication with said rotatable transfer means and including a second photosensitive device located for successive alignment with each said aperture and said container opening associated therewith for deriving a second output signal upon exposure to light passing through said container defects;

first light source means for illuminating the exterior of containers when passing said first inspection station means;

second light source means for illuminating the exterior of containers when passing said second inspection station means;

infeed means for feeding containers intermediate said holder means retention components and said transfer means contact surfaces;

discharge means normally operative to receive each said container when said holder means reciprocative retention component contact member associated therewith is retracted and actuable to negate said container reception;

control means responsive to said first or second output signal for actuating said discharge means to negate said reception of a defect containing container;

drive means for drivably rotating said first shaft; said first light source means configured for principally illuminating the sidewall portion of a said container which is leading with respect to the direction of movement thereof when passing said first inspection station means; and said second light source means is configured for principally illuminating the sidewall portion of a said container which is lagging with respect to the direction of movement thereof when passing said second inspection station means.

2. The apparatus of claim 1 in which said first light source means is configured for principally illuminating the sidewall portion of a said container which is leading with respect to the direction of movement thereof when passing said first inspection station means.

3. The apparatus of claim 1 in which said first light source means comprises two lamps mounted upon said frame adjacent said first inspection station means, one said lamp being positioned below and the other said lamp above the path of movement of said containers.

4. The apparatus of claim 3 in which each said lamp is a quartz variety rated at about 300 watts.

5. The apparatus of claim 1 in which said second light source means comprises two lamps mounted upon said frame adjacent said second inspection station means, one said lamp being positioned below and the other said lamp above the path of movement of said containers.

6. The apparatus of claim 5 in which each said lamp is a quartz variety rated at about 300 watts.

7. The apparatus of claim 1 wherein:
said first shaft is generally horizontally disposed;
said first inspection station means first photoresponsive device comprises an array of photodiodes the center of which is substantially aligned with a first radius extending 22.5° away from vertical center of said first shaft; and
said second inspection station means second photoresponsive device comprises an array of photodiodes the center of which is substantially aligned with a second radius extending 22.5° away from vertical center of said first shaft in a direction opposite said first radius.

8. The apparatus of claim 1 in which said discharge means comprises:
a second shaft rotatably supported upon said frame and having an axis of rotation parallel with said first shaft axis;
discharge transfer wheel means fixed to and rotatable with said second shaft and having an outer periphery configured to define a sequence of regularly spaced generally arcuately shaped container cradles corresponding in number with the number of said apertures for receiving said containers from said holder means and carrier means at a receiving position following said retraction of an associated said contact member, said discharge transfer wheel means moving said cradles from said receiving position to a discharge position.

9. The apparatus of claim 8 wherein each said discharge transfer wheel means cradle arcuate shape includes a region of radius substantially corresponding with the radius of a said container sidewall portion.

10. The apparatus of claim 8 wherein said discharge means further comprises discharge chute means for receiving said containers from said container cradles at said discharge position.

11. The apparatus of claim 8 wherein;
said first shaft is generally horizontally disposed; and
said second shaft is located below said first shaft so as to receive released containers during free downward movement thereof.

12. The apparatus of claim 8 in which said discharge transfer wheel means includes retention means associated with each said cradle, having a normally active condition retaining received said containers and having a passive condition not retaining received said containers upon said discharge means actuation.

13. The apparatus of claim 12 in which said retention means comprises:

a vacuum port positioned within each said cradle in the vicinity of the said arcuately shaped portion thereof; and passage means for selectively communicating each said vacuum port with a vacuum source when said cradle associated with said vacuum port moves from said receiving position to said discharge position.

14. The apparatus of claim 13 in which said retention means further comprises valve means actuable by said control means for selectively terminating said passage means communication with said vacuum source.

15. The apparatus of claim 14 in which said retention means valve means includes a solenoid energizable by said control means to effect said actuation.

16. The apparatus of claim 14 wherein said passage means includes:
a first array of passages extending to said vacuum ports located in alternate ones of the said sequence of said cradles spaced about said outer periphery;
a second array of passages extending to said vacuum ports located in said cradles other than said alternate ones of said sequence; and
said valve means is configured for separately effecting said select termination for each said first and second array passages.

17. The apparatus of claim 14 wherein said retention means includes:
vacuum manifold means fixed to said discharge transfer wheel means and having an outwardly disposed surface within which are formed slots of predetermined length, each said slot communicating with a unique passage of said passage means extending to a unique said vacuum port;
suction port means fixed to said frame, having a transfer surface of predetermined extent in slideable contact with said manifold means outwardly disposed surface and having a transfer opening communicating with said vacuum source, positioned for intermittent vacuum communicating alignment with said slots;
said valve means terminating said communication between said transfer opening and said vacuum source when actuated.

18. The apparatus of claim 17 in which:
said passage means includes a first array of passages extending to said vacuum ports located in alternate ones of the said sequence of said cradles spaced about said outer periphery and a second array of passages extending to said vacuum ports located in said cradles other than said alternate ones of said sequence;
said vacuum manifold means outwardly disposed surface slots are provided as a first group thereof communicating with said first array of passages, and a second group thereof radially inwardly disposed from said first group and communicating with said second array of passages;
said suction port means transfer surface is configured having first and second said transfer openings positioned for alignment, respectively, with said first and second groups of vacuum manifold means slots.

19. The apparatus of claim 18 wherein said valve means comprises:
a first slide valve operatively associated with said first transfer opening and a second slide valve operatively associated with said second transfer opening; and
first and second actuation means operatively associated with respective said first and second slide valves for effecting said communication termination by actuation of said first and second slide valves.

20. The apparatus of claim 1 in which said holder means reciprocative retention components are configured to extend said contact members into nonyieldable abutting engagement with a said container bottom portion.

21. The apparatus of claim 1 in which said holder means comprises:
holder wheel means having a hub portion and a connecting surface fixed to said first shaft for rotation therewith about said axis of rotation thereof;
cam means fixed to said supportive frame and having a generally annular shaped cam profile portion;
said reciprocative retention components comprise:
a plurality of slide housing members removably attached to said holder wheel means connecting surface, generally aligned about predetermined radii spaced in correspondence with said carrier means apertures and extending from said first shaft axis of rotation; and
carriage means mounted for reciprocative movement within each said slide housing member for fixedly supporting a said contact member in position to selectively effect said abutting engagement, and including cam follower means fixed thereto and operatively associated with said cam means cam profile portion.

22. The apparatus of claim 21 in which said cam means profile portion is generally coaxially disposed about said first axis.

23. The apparatus of claim 22 in which said cam means profile portion is located radially inwardly of said slide housing members.

24. The apparatus of claim 23 in which said carriage means cam follower means comprises:
first and second stud means fixed to said carriage means and having portions generally radially inwardly depending therefrom;
first and second roll cam followers rotatably mounted upon said respective first and second stud means inwardly depending portions and mutually positioned to straddle said cam profile portion in continuous, positive rolling engagement.

25. The apparatus of claim 24 in which said first stud means is selectively manually rotatable about a given axis and configured to support said first roll cam follower in eccentric fashion with respect to said given axis so as to provide adjustment thereto effecting said positive rolling engagement.

26. The apparatus of claim 21 in which said holder wheel means connecting surface is configured having a plurality of outwardly extending slots for receiving said slide housing members in nesting relationship for effecting said radical alignment thereof.

27. The apparatus of claim 26 in which:
said holder wheel means hub portion is configured having a plurality of alignment surfaces corresponding in number with said plurality of slide housing members for providing a generally radially aligning abuttable contact with said slide housing members.

28. The apparatus of claim 27 in which said holder means includes a plurality of keeper means corresponding in number with said plurality of slide housing members, removably attached to the radially outward periphery of said holder wheel means and each being abuttably engageable with a corresponding said slide housing member to assure the said aligning abuttable contact thereof with said hub portion alignment surfaces.

29. The apparatus of claim 21 in which said carriage means includes slide pin means fixed thereto and slideably engageable within an associated said slide housing member.

30. The apparatus of claim 21 in which:
each said slide housing member includes a gib having a generally radially outwardly extending keyway; and
each said carriage means includes a generally radially inwardly extending key means slideably engageable within said keyway for providing transverse support to said carriage means.

31. The method of testing open-ended containers for defects in the form of openings in their structure, said containers having an opening surmounted by a rim and a sidewall portion extending from said rim to a bottom portion, comprising the steps of:
positioning said openings of a continuous sequence of said containers over apertures extending through a rotating test carrier and defining a predetermined locus of movement of said apertures;
compressibly retaining said container rim in light-tight relationship against said rotating carrier by applying a contact member against said container bottom portions;
providing a first light detecting device at a first station positioned adjacent said rotating carrier at said locus of movement, the interior of a said container being exposed to said first light detecting device through a said aperture when moved across said first station;
illuminating principally the sidewall portion of a said container leading with respect to the direction of said locus of movement when said container is moved across said first station;
generating a first output signal in response to light passing through a said defect and impinging upon said first light detecting device;
providing a second light detecting device at a second station positioned adjacent said rotating carrier at said locus of movement, the interior of a said container being exposed to said second light detecting device through a said aperture when moved across said second station;
illuminating principally the sidewall portion of a said container lagging with respect to the direction of said locus of movement when said container is moved across said second station;
generating a second output signal in response to light passing through a said defect and impinging upon said second light detecting device; and
sorting containers having a detected said defect from those not having a detected said defect in response to said first or second output signals.

32. The method of claim 31 wherein said sorting step includes the steps of:
providing a discharge carrier adjacent said test carrier normally operative to receive and retain said containers for movement to a discharge station; and
releasing said contact member from said container bottom portion to remove said compressive retention as said container approaches said discharge carrier to permit the free movement thereof into said discharge carrier.

33. The method of claim 30 including the step of negating the said normal operation of said discharge carrier to receive said containers in response to said first or second output signals.

34. The method of claim 33 in which:
said normally operative retention of said containers by said discharge carrier is by the application of vacuum to the said sidewall thereof through a vacuum port engageable therewith, whereby containers having deformed sidewalls are not received by said discharge carrier; and
said step of negating said normal operation of said discharge carrier is carried out by preventing said application of vacuum to said container sidewall.

35. The method of claim 32 in which said normally operative retention of said containers by said discharge carrier is by the application of vacuum to the said sidewalls thereof through a vacuum port engageable therewith, whereby containers having deformed sidewalls are not received by said discharge carrier.

36. Apparatus for testing open-ended containers for defects in the form of openings in their structure, said container having an open end surmounted by a rim, a sidewall portion extending from said rim to a bottom portion, said apparatus comprising:
means defining a supportive frame;
a shaft rotatably supported upon said frame and having a generally horizontally disposed axis of rotation;
drive means for drivably rotating said shaft;
carrier disk means fixed to and rotatable with said shaft, having a predetermined number of apertures therein uniformly mutually and symmetrically spaced a predetermined distance apart about a circular locus of movement thereof and configured in conrrespondence with the configuration of said container rim for receiving said containers in abuttive relationship at a contact surface disposed about the periphery of each said aperture;
holder means including a plurality of reciprocative retention components corresponding in number with the number of said apertures, mounted for rotation at said shaft, each positioned at a location spaced from and disposed opposite a corresponding said aperture, each said retention component including a contact member extensible into engagement with a said container bottom portion to urge the rim thereof into light-tight abutting engagement with a said contact surface, and retractable to release said container;
first inspection station means mounted upon said frame adjacent to, stationary with respect to and in light-tight communication with said transfer disk means and including a first photosensitive device located for successive alignment with each said aperture and said container opening associated therewith for deriving a first output signal upon exposure to light passing through a said container defect;
second inspection station means, spaced from said first inspection station means a distance corresponding to said predetermined distance between said apertures or a select multiple thereof, mounted upon said frame adjacent to, stationary with respect to and in light-tight communication with said transfer disk means and including a second photosensitive device located for successive alignment with each said aperture and a said container opening associated therewith for deriving a second output signal upon exposure to light passing through a said container defect;

light source means for selectively illuminating the exterior of said container when passing said first and second inspection station means;

infeed means for feeding containers intermediate said holder means retention components and associated said contact surfaces;

discharge means normally operative to receive each said container at a predetermined position when said holder means reciprocative retention component contact member associated therewith is retracted and actuable to negate said container reception; and control means comprising:

encoder means responsive to said shaft rotation for deriving a clock signal corresponding with the position of each said aperture as it passes a predetermined reference position;

first AND logic means responsive to said first output signal and said clock signal for deriving a first defect signal;

second AND logic means responsive to said second output signal and said clock signal for deriving a second defect signal;

sequential storage means responsive to said clock signal, having a first input zone for receiving said first defect signal and a first output for deriving said first defect signal in time synchronization correspondence with said distance between said first and second inspection station means;

OR logic means responsive to said time synchronized first detect signal and/or said second defect signal for providing an OR logic output;

said sequential storage means further including a second input zone for receiving said OR logic output and a second output for deriving a composite defect signal in time synchronism correspondence with the distance between said second inspection station means and said discharge means predetermined position; and switching network means responsive to said composite defect signal for actuating said discharge means.

37. The apparatus of claim 36 including:

counter means responsive to said clock signal for deriving a cycle signal corresponding substantially with each complete revolution of said shaft; and said first and second photosensitive devices resettable in response to said cycle signal.

38. The apparatus of claim 37 in which:

said counter means is configured to provide binary output signals corresponding with the position of each said aperture with respect to said reference position; and including first readout means responsive to said binary output signals, said clock signal and said composite defect signal for providing a visual indicia representing that aperture against which a container having a defect is positioned.

39. The apparatus of claim 37 including sequential defect counter means responsive to said composite defect signal for providing a cumulative total of the number of containers having a detected defect.

40. The apparatus of claim 37 including lamp means coupled with said first and second photosensitive devices and responsive to said first and second output signals for providing a transient visible indicia representing a detected container defect.

* * * * *